United States Patent
Atanackovic

(10) Patent No.: US 10,656,088 B2
(45) Date of Patent: May 19, 2020

(54) ULTRAVIOLET BIOSENSOR

(71) Applicant: Silanna UV Technologies Pte Ltd, Singapore (SG)

(72) Inventor: Petar Atanackovic, Henley Beach South (AU)

(73) Assignee: Silanna UV Technologies Pte Ltd, Singapore (SG)

(*) Notice: Subject to any disclaimer, the term of this patent is extended or adjusted under 35 U.S.C. 154(b) by 214 days.

(21) Appl. No.: 15/664,375

(22) Filed: Jul. 31, 2017

(65) Prior Publication Data
US 2018/0042511 A1 Feb. 15, 2018

Related U.S. Application Data

(60) Provisional application No. 62/374,216, filed on Aug. 12, 2016.

(51) Int. Cl.
*G01N 21/63* (2006.01)
*H01L 29/66* (2006.01)
(Continued)

(52) U.S. Cl.
CPC ............ *G01N 21/63* (2013.01); *G01N 21/76* (2013.01); *G01N 33/53* (2013.01);
(Continued)

(58) Field of Classification Search
CPC .... G01N 21/00; G01N 21/6586; G01N 21/76; G01N 27/00; G01N 33/53; G01N 21/63;
(Continued)

(56) References Cited

U.S. PATENT DOCUMENTS 4,238,757 A 12/1980 Schenck
4,777,019 A 10/1988 Dandekar
(Continued)

FOREIGN PATENT DOCUMENTS

WO 2013147388 A1 10/2013

OTHER PUBLICATIONS

Mustafa H. Chowdhury et al., "Aluminum Nanoparticles as Substrates for Metal-Enhanced Fluorescence in the Ultraviolet for the Label-Free Detection of Biomolecules", 2009, Analytical Chemistry, 81, 1397-1403 (Year: 2009).*
(Continued)

*Primary Examiner* — Jill A Warden
*Assistant Examiner* — Quocan B Vo
(74) *Attorney, Agent, or Firm* — MLO, a professional corp.

(57) ABSTRACT

In some embodiments, a semiconductor biosensor includes a plurality of wells, a plurality of detectors, and processing circuitry. Each well is configured to hold a test sample and to allow the test sample to be irradiated with ultraviolet radiation. The plurality of detectors are configured to capture a spectral response of the test sample irradiated with the ultraviolet radiation. Each well is coupled directly onto a detector, and each detector includes a) a photodiode and b) a planar optical antenna tuned to a particular wavelength. The planar optical antenna is between the photodiode and the well. The processing circuitry is coupled to the plurality of detectors, the processing circuitry being configured to calculate an average spectral response for the plurality of detectors.

19 Claims, 30 Drawing Sheets

(51) Int. Cl.
  *H01L 31/105* (2006.01)
  *H01L 31/0232* (2014.01)
  *H01L 31/0392* (2006.01)
  *H01L 31/0224* (2006.01)
  *H01L 27/144* (2006.01)
  *G01N 33/53* (2006.01)
  *G01N 21/76* (2006.01)

(52) U.S. Cl.
  CPC .... *H01L 27/1446* (2013.01); *H01L 29/66136* (2013.01); *H01L 31/02327* (2013.01); *H01L 31/022416* (2013.01); *H01L 31/03921* (2013.01); *H01L 31/105* (2013.01); *Y02E 10/50* (2013.01)

(58) Field of Classification Search
  CPC . H01L 21/00; H01L 29/772; H01L 29/66136; H01L 27/1446; H01L 31/022416; H01L 31/03921; H01L 31/02327; H01L 31/105; C12Q 1/00; Y02E 10/50; A61N 2007/0004; A61B 5/053; A61B 8/00
  See application file for complete search history.

(56) References Cited

U.S. PATENT DOCUMENTS

| | | |
|---|---|---|
| 6,448,064 B1 | 9/2002 | Vo-Dinh et al. |
| 6,579,721 B1* | 6/2003 | Natan ................ C12Q 1/6825 356/445 |
| 6,743,581 B1 | 6/2004 | Vo-Dinh |
| 7,429,492 B2 | 9/2008 | Lin et al. |
| 7,692,219 B1 | 4/2010 | Holm-Kennedy |
| 7,738,086 B2 | 6/2010 | Shepard et al. |
| 8,022,444 B2 | 9/2011 | Kim et al. |
| 8,518,329 B2 | 8/2013 | Hassibi et al. |
| 8,540,866 B2 | 9/2013 | Rothberg et al. |
| 8,668,871 B2 | 3/2014 | Matsumoto et al. |
| 8,735,077 B2 | 5/2014 | Shim et al. |
| 8,860,442 B2 | 10/2014 | Je et al. |
| 8,962,376 B2 | 2/2015 | Atanackovic et al. |
| 8,969,781 B2 | 3/2015 | Hassibi et al. |
| 8,999,739 B2 | 4/2015 | Afzali-Ardakani et al. |
| 2005/0053974 A1* | 3/2005 | Lakowicz .......... G01N 21/4788 435/6.12 |
| 2006/0210279 A1* | 9/2006 | Hillis ..................... B82Y 20/00 398/118 |
| 2007/0097364 A1 | 5/2007 | Shepard et al. |
| 2009/0317917 A1 | 12/2009 | Klapproth et al. |
| 2010/0248284 A1 | 9/2010 | Chen et al. |
| 2010/0270174 A1 | 10/2010 | Chen et al. |
| 2010/0300899 A1 | 12/2010 | Levine et al. |
| 2011/0170103 A1* | 7/2011 | Gomez Rivas .... G01N 21/6428 356/445 |
| 2011/0204872 A1 | 8/2011 | Gridelet et al. |
| 2012/0049242 A1* | 3/2012 | Atanackovic ... H01L 31/022441 257/184 |
| 2013/0004967 A1* | 1/2013 | Halverson ........... B01L 3/50853 435/7.8 |
| 2013/0309135 A1 | 11/2013 | Park et al. |
| 2015/0116484 A1* | 4/2015 | Kim ...................... G01N 21/76 348/135 |
| 2015/0141267 A1* | 5/2015 | Rothberg ............. C12Q 1/6869 506/2 |
| 2015/0323385 A1* | 11/2015 | Han ......................... G01J 3/36 356/300 |
| 2017/0199078 A1* | 7/2017 | Huang .................. H01L 31/107 |

OTHER PUBLICATIONS

Michael B. Ross et al. "Aluminum and Indium Plasmonic Nanoantennas in the Ultraviolet", 2014 ACS Publications, The Journal of Physical Chemistry, 118 (23), 12506-12514 (Year: 2014).*

Evarts, Smartphone, Finger Prick, 15 Minutes, Diagnosis—Done, Columbia Engineering, Feb. 4, 2015, Accessed Online on Feb. 25, 2015, http://engineering.columbia.edu/smartphone-finger-prick-15-minutes-diagnosis—done-0.

Moore, Engineers have created a smartphone HIV test that costs $35 to make, Gigaom, Feb. 22, 2017, Accessed on Feb. 25, 2015, https://gigaom.com/2015/02/22/engineers-have-created-a-smartphone-hiv-test-that-costs-35-to-make/.

* cited by examiner

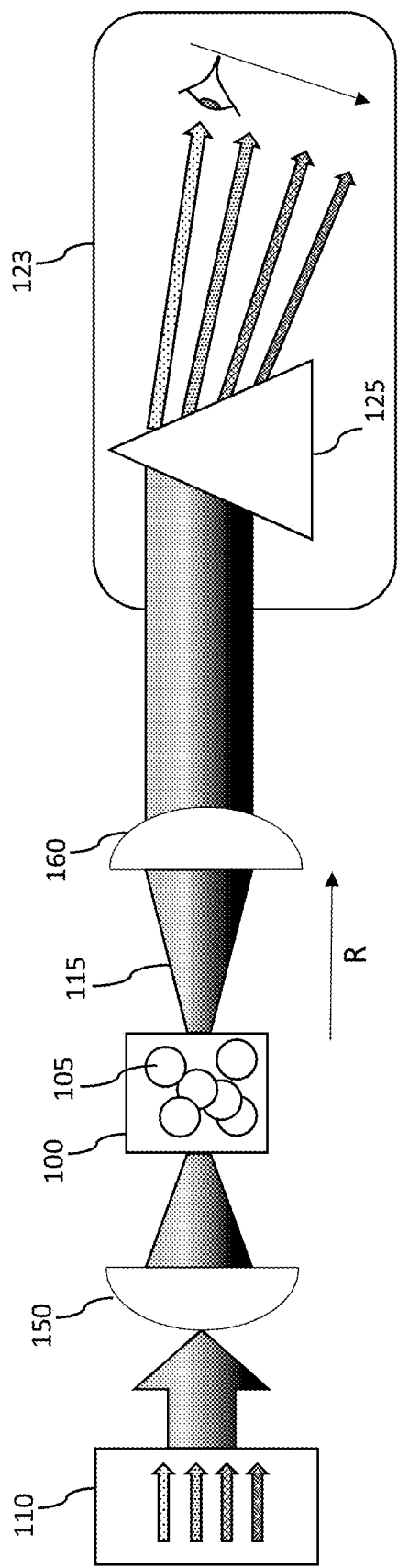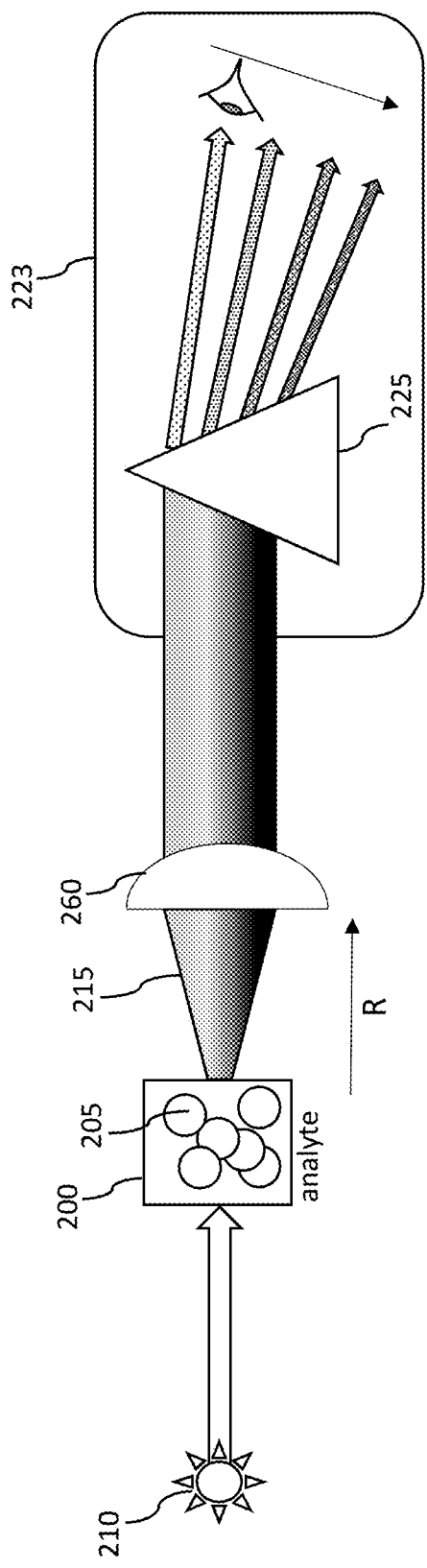
FIG. 3A (Prior Art)
FIG. 3B (Prior Art)

ULTRAVIOLET BIOSENSOR

RELATED APPLICATIONS

This application claims priority to U.S. Provisional Patent Application No. 62/374,216, filed on Aug. 12, 2016 and entitled "Fluorescence Biosensor"; which is hereby incorporated by reference in its entirety.

BACKGROUND

Biosensing devices for detection of biological or chemical components have become widely used in many applications such as medical diagnostic laboratories, point-of-care settings, and field work. The utility of such devices in point-of-care testing has grown rapidly due to the benefits of providing portable and immediate results to assist in clinical management decisions of early detection and disease screening. Biosensor applications have advanced with recent developments in biomolecular chemistry technologies which provide reagents with improved selectivity and affinity to specific biological targets, such as specific disease markers expressed by proteins, antibodies and nucleic acid fragments or DNA and the like.

A primary function of a biosensor is to provide an output corresponding to the quantitative detection of the presence and/or relative abundance of a specific target biomolecule in a given analyte. The analyte can be presented to the biosensor either in-vivo or in-vitro to the source or patient. Enzyme-linked immunosorbent assay tests (ELISA) are one category of biosensors, in which a target biomolecule can be detected for presence and quantified within an analyte volume. In general, a glass plate is prepared with an array of identical analyte volumes or wells. Within each of the wells a specific bioreceptor is attached to the inner surface of the glass wells with a known concentration. The bioreceptors are typically either an antibody (Ab) or an antigen (Ag)—and the Ag-Ab pair is preselected with criteria for high selectivity and affinity to a target biomolecule under test. An analyte comprising the material under test is then titrated in each well to a predetermined concentration matrix and allowed to react with the specific bioreceptors. The analyte comprises the complementary substance to the particular bioreceptor that is used. If the target species is present in the analyte it will be immobilized and bound to the bioreceptor. Bioreceptors can be developed to produce a physical change indicating the binding event or a subsequent reagent can be passed over the wells to reveal the result.

In general, the ELISA sequence is engineered so that an optical indicator results when a successful binding event occurs. The degree to which the target within the analyte binds to the bioreceptors is detected optically as either a change of color or optical density. The magnitude of the optical response is directly proportional to and representative of the number density of the target biomolecule within each well. The optical response of each of the wells is typically measured using an optical sensor that measures the optical intensity or power due to the absorption or fluorescence signal. The optical sensor may also be tuned to a specific wavelength or wavelength range. The optical sensor may also capture an image of the entire plate comprising an M×N array of wells (typically, M and N are integers characterizing the assay configuration of the wells with standard sizes of M×N=96, 384 and 1536 wells). For example, the test plate optical response can be directly mapped using a digital charge-coupled device (CCD) array. Furthermore, if more than one bioreceptor is utilized within each well it is possible to produce a specific and unique wavelength response for each particular antigen-bioreceptor event type, thereby producing improved throughput for the diagnostic test via the use of optical multiplexing. A wavelength selective sensor is beneficial for this purpose. The two main types of optical responses used to probe the antigen-photoreceptor binding event are: (i) optical absorption and (ii) optical excitation fluorescence. Others are also possible, such as, electrically stimulated fluorescence. It is well known in prior art that optical techniques enable large ensembles of such arrays to be processed with high throughput. The trade-off to throughput and array size is typically due to the lower limit of sensitivity for detection of the target binding event.

The use of optical interrogation of the described test array necessarily requires an optical sensor to be spaced at a distance from the plate to enable collection of light or optical imaging of the well or array. That is, imaging and focusing optics are required to probe the regions of interest and provide directed optical energy to a receiving optical sensor for measurement. The sensitivity of the optical detection process is therefore limited by the analyte volume contained in each well, the optical cross-section presented by the binding event through absorption or fluorescence, the transparency of the materials comprising the array, and the etendue limit of the optical system used.

Yet a further class of biosensor measurement systems require the quantification of the unique optical wavelength absorption spectrum or fluorescence emission spectrum of a particular analyte. So-called, label-free detection of target biomolecules is becoming of increasing utility for biomolecular sensors. Resolving the wavelength response of target biomolecule species within an analyte further requires the use of at least one of a wavelength spatially dispersive element, such as, a refractive prism or diffractive grating. These dispersive wavelength spectroscopic methods further increase the complexity of the biosensing apparatus and reduce the light collection to the optical sensor, thereby increasing the optical lower limit of sensitivity.

Biosensing of biomolecules for medical research, such as proteins and DNA, may also be characterized by their ultraviolet spectral absorption or fluorescence spectrum. In such devices, a sample is subjected to ultraviolet light and the output sensed with a detector. In some devices, a specific wavelength is selected from the source, and the sample is swept with varying wavelengths to characterize the response of the sample. In other devices, the sample is subjected to a broad spectrum and a dispersive or wavelength selective filter is used to select a particular wavelength to be analyzed by the detector. In either type, a single detector is used, which is broadly sensitive. In addition, the light collection optical path requires distance between the analyte and the detector, which limits the sensitivity of the device.

As biosensors continue to be more widely used, there is a continuing need for improved functionality and lower cost devices.

SUMMARY

In some embodiments, a semiconductor biosensor includes a plurality of wells, a plurality of detectors, and processing circuitry. Each well is configured to hold a test sample and to allow the test sample to be irradiated with ultraviolet radiation. The plurality of detectors are configured to capture a spectral response of the test sample irradiated with the ultraviolet radiation. Each well is coupled directly onto a detector, and each detector includes a) a photodiode and b) a planar optical antenna tuned to a particular wavelength. The planar optical antenna is between the photodiode and the well. The processing circuitry is coupled to the plurality of detectors, the processing circuitry being configured to calculate an average spectral response for the plurality of detectors.

In some embodiments, a biosensing device includes a well and a detector. The well is configured to hold a test sample and to allow the test sample to be irradiated with ultraviolet radiation. The detector has a photodiode and a planar optical antenna coupled to the photodiode. The well is coupled directly to the detector, with the planar optical antenna being between the photodiode and the well. The planar optical antenna has a structure in or on a plane of the planar optical antenna, the structure having dimensions configured to tune the planar optical antenna to a particular wavelength.

BRIEF DESCRIPTION OF THE DRAWINGS

FIG. 3A-3B illustrate the spatial optical configuration of dispersive-type spectrometers known in the art.

DETAILED DESCRIPTION OF THE EMBODIMENTS

Figure 1:
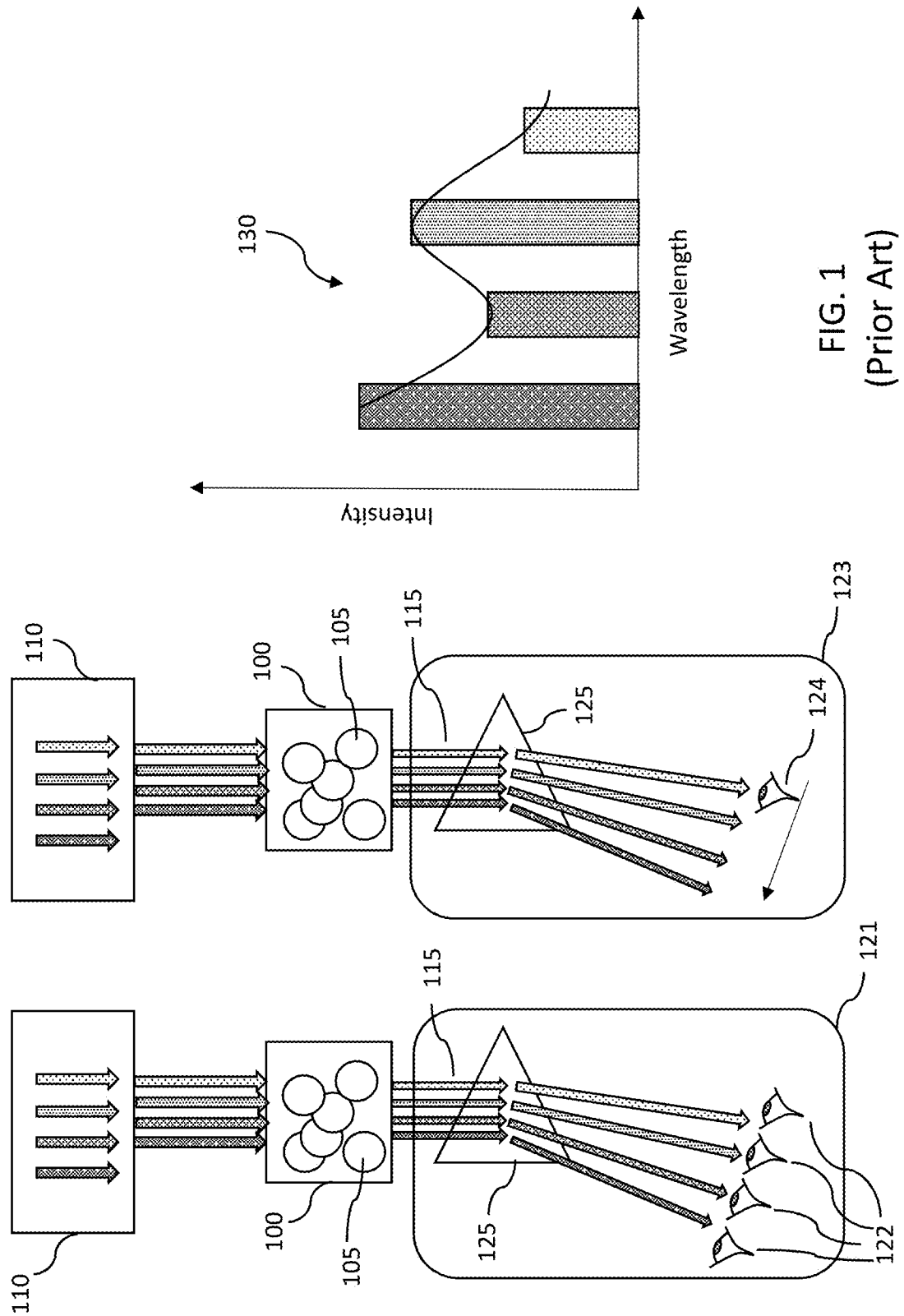
FIG. 1 is a schematic of dispersive spectral detection known in the art, using absorption.

Reference now will be made in detail to embodiments of the disclosed invention, one or more examples of which are illustrated in the accompanying drawings. Each example is provided by way of explanation of the present technology, not as a limitation of the present technology. In fact, it will be apparent to those skilled in the art that modifications and variations can be made in the present technology without departing from the scope thereof. For instance, features illustrated or described as part of one embodiment may be used with another embodiment to yield a still further embodiment. Thus, it is intended that the present subject matter covers all such modifications and variations within the scope of the appended claims and their equivalents.

Biosensors are disclosed herein that use fluorescence detection or change in optical density on a substantially semiconductor platform, with high sensitivity and without the need for testing in a lab, thus reducing cost. These devices provide compact bio-analysis on a single chip, with high throughput screening of biomaterials. The devices utilize planar optical antennas which serve as filters for ultraviolet (UV) light, such as in the deep ultraviolet range. The optical antennas may be aluminum-based, aluminum-dielectric and aluminum-semiconductor based that are capable of uniquely tailoring their optical response for the deep UV range. Benefits include: (i) a lithographically patterned substantially planar optical device responsive to the extreme ultraviolet optical spectrum 180-400 nm; (ii) efficient product utilization (e.g., analyte sample volumes on the order of nanoliter nL and picoliter pL and femtoliter fL); (iii) label-free target analysis; (iv) highly cascadable bio-chips for reaction pathway analysis; and (v) light-activated reaction pathway bio-chip reactors. The biosensors can provide, for example, detection of bacteria such as E. Coli and spores, and on smaller length scale than detection of AGCT nucleotide sequences, and also enable real-time monitoring for the molecular assembly of complex molecules and or genomes.

The present ultraviolet biosensors incorporate spectrometers immediately beneath and close to an analyte sample, the proximity of the spectrometer and the analyte resulting in a device with higher sensitivity than conventional dispersive type biosensors. The spectrometers are responsive to different wavelengths, and the magnitude of detection at a particular wavelength provides the characterization of the analyte. In some embodiments, the substance under test may exhibit a particular spectral response when irradiated with UV radiation of a particular wavelength. That fluorescence may then be detected by the spectrometers to characterize the sample under test. In other embodiments, the biosensor may detect the absorption response of the test sample when irradiated with UV light. Thus, the present biosensing devices may detect a spectral response of a test sample, where the spectral response is created in an absorption mode or an excitation fluorescence mode.

FIG. 1 shows a general representation of a dispersive type of spectroscopic biosensor known in the art, using an absorption process. In these absorption detectors, an analyte sample 100 to be tested is subjected to an input wavelength spectrum 110. Input wavelength spectrum 110 is shown with four wavelengths for illustrative purposes, where the wavelengths may represent, for example, blue, green, yellow and red. The analyte 100 is characterized by the measured wavelength spectrum 115 that is output after the input spectrum 110 has passed through the analyte 100. A single analyte volume containing an ensemble of target biomolecules 105 is optically excited or probed, where the measured spectrum to be resolved is detected on one or more detectors 122, 124. The prism 125 represents an optically dispersive component that accepts collinear propagating wavelengths and spatially disperses specific wavelengths to known spatial positions in a measurement plane containing at least one detector. For example, the wavelength dispersive detector 121 can measure the output spectrum by taking a snapshot of all the wavelengths at once, such as with a plurality of detectors 122 in the detection plane calibrated to specific wavelengths. The measurement can also be achieved by scanning the output spectrum as shown in wavelength dispersive detector 123, where each wavelength is detected one at a time using a single detector 124. The measured wavelength spectrum of the output spectrum 115 is shown in graph 130, where wavelengths with lower intensity result from higher absorption by the analyte 100.

Figure 2:
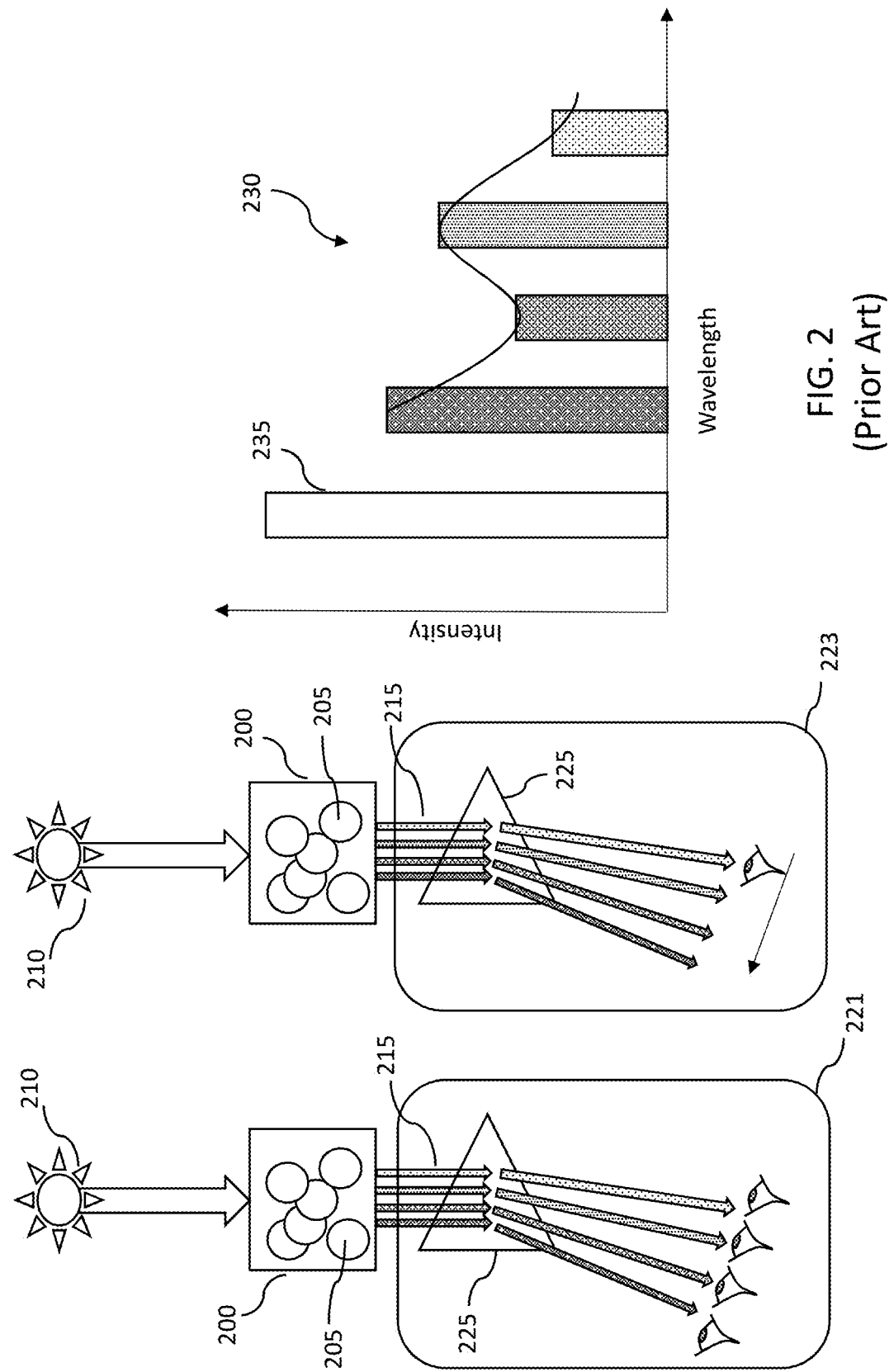
FIG. 2 is a schematic of dispersive spectral detection known in the art, using fluorescence excitation.

FIG. 2 shows another known type of dispersive wavelength spectrum measurement, using excitation fluorescence. In this type of sensor, the analyte 200 is subjected to an excitation energy 210 (input light, typically higher in energy than the spectral band of interest), which causes the analyte 200 with target biomolecules 205 to emit a characteristic output spectrum 215. The output spectrum 215 is spatially dispersed into specific wavelengths by an optically dispersive component represented by prism 225. The measured wavelength spectrum can be determined by a snapshot type of detector 221 or a scanning type of detector 223, as described in FIG. 1. The measured wavelength spectrum is shown in graph 230, where the excitation energy 210 is represented by wavelength 235.

FIGS. 3A-3B show diagrams representing spatial optical configurations for known dispersive-type spectrometers including light collection optics. In the absorption spectrum method of FIG. 3A, a focus optic 150 is used to focus a known input spectrum 110 comprising a plurality of wavelengths. The analyte 100 comprising the target biomolecules 105 (if present) absorbs at least a portion of the incident spectrum. The change in optical density can be correlated to the number density of a target biomolecule or collection thereof. The output spectrum 115 emerging from the analyte volume 100 is collected by a light collection optic 160 and is required to direct the output spectrum 115 to the wavelength dispersive detector 123. Note that due to Mie scattering process of biomolecules within the analyte 100, the light collection can be improved advantageously by use of an appropriate light collection optic 160. The detection components of FIGS. 3A-3B include the light collection optic 160/260 and the detector 123/223. The wavelength dispersive detector 123 is illustrated as a scanning type in this illustration, but can also be snapshot type as described above in relation to FIG. 1. For the case of the excitation fluorescence method shown in FIG. 3B, an optional optic is used for the input light 210 and can be incoherent or coherent light supplied by an LED or laser diode. The absorbed high energy excitation light in the target biomolecules 205 (if present) of the analyte 200 re-radiate an emission spectrum 215 (typically of lower energy than the excitation energy 210). In general biomolecules radiate fluorescence in a plurality of angles (averaging $4\pi$ steradians) depending upon their preferred axis and orientation relative to the incident excitation light. The light collection optic 260 again is needed to direct at least a portion of the solid angle emitted by the fluorescing biomolecules and thus optically coupling the output spectrum 215 to the detector 223.

The change in spectral signature or optical density within a preselected wavelength range may be detected by a monochromatic light reader consisting of an optical detector and a light source, such as a light emitting diode (LED) or laser diode (LD). For biosensing applications, the use of an ultraviolet light source operating in the 180-280 nm range or the well-known UVC band is desirable. In prior art applications, in general each distinct well in the glass plate is optically read by an associated source and detector. In general, a single source and a single detector is utilized for reading the wells sequentially contained within the optical plate substrate. More than one well can be read by using an imaging system coupled to a solid-state camera array, namely, a charge coupled device (CCD) array. The detection components are spaced by the distance R (from analyte 100/200 to light collection optic 160/260 in FIGS. 3A-3B) from the glass plate/well in order to achieve the proper optical focusing to capture a given emitted solid angle of light $\Omega_e$ from the well. Simplistically, the detector-well spacing R reduces the intensity of light captured by the detector $I_{Det}$ and is governed by the inverse square law of irradiance (i.e., $I_{Det}$ is directly proportional to $1/R^2$). For application to UVC optical detection, it is also important that the glass plate be optically pure and chemically inert so as not to adversely affect the process. Such plates are expensive and typically manufactured using high purity silica glass, high alumina content Silica glass or sapphire. While the assay plates can be cleaned after each use they are typically single use and disposable. Commercially available glass plates range in standard well volumes of 100-400 microliter per well (96 well assay plate), 50-100 microliter per well (384 well assay plate) and ~10-12.5 microliters per well for a 1536 well assay plate. Robotic sample preparation and the need for performing more tests per standard plate area (where a standard format plate area is typically ~85×10 mm) is enabling a reduction in the cost per test and thereby forcing the trend of total well number per plate to increase and the individual well volumes to decrease.

In either the absorption or fluorescence type of sensor of FIGS. 1-3, the distance R between the analyte (100, 200) and the light collection optic (160, 260) is significant in prior art methods, such as on the order of millimeters, centimeters, or even meters. The amount of detected light is inversely proportional to the distance squared between the analyte and detector; that is, the farther the distance from the test sample, the lower the sensitivity. Thus, conventional sensors are limited in their light collection ability and thus ultimately in the sensitivity of the system. A simple method to overcome this limitation with high values of R is the use of relatively large amounts of analyte (and thus high number density of target biomolecules such as on the order of 10's of microliters to milliliters. Furthermore, high intensity excitation is used to increase the signal-to-noise ratio of the absorption or fluorescence spectrum.

Therefore, in light of the above discussion, an improvement over the prior art biosensors can be achieved by reducing the distance of the detector from the analyte volume and reducing the physical losses and dimensions always present when using dispersive type spectrometers. Typically, a measurement that is capable of providing high sensitivity for a given binding event enables smaller analyte volumes to be utilized and enables detection of smaller antigen concentrations within an analyte. By increasing detection sensitivity in the present embodiments, the sample volumes can be further reduced thereby increasing dramatically the throughput for a given prepared plate. That is, the cost per test can be reduced if the sensitivity of detection can be increased. There is also a pressing need to improve over the prior art to specifically increase the number of functions performed per test in order to further reduce the total test cost. Thus, improving the sensitivity of detecting biomarkers over the prior art enables significantly reduced analyte volumes to be used and thus higher throughput, as well as enabling compact test systems.

Ultraviolet Biosensors

Biosensors having ultraviolet-tuned optical antennas for biomolecular spectral sensing will now be disclosed. In particular, the deep ultraviolet range (DUV) is used as this is the region of interest for biosensing. For example, DUV excited fluorescence detection may be used for bacteria (250-400 nm), DNA (200-290 nm), determining OH hydroxyl production (308 nm) and excimer UV excitation (170-222 nm). Silicon has a useful UV responsivity in the 200-400 nm wavelength range, and thus spectrally resolving 200-400 nm fluorescence is well suited to optoelectronic photodetectors constructed from at least one of bulk Si or silicon-on-insulator (SOI)/silicon-on-sapphire (SOS) platforms. Conventionally, methods using optical bandpass filters comprising multilayered dielectric materials typically suffer high loss, use expensive materials (for example fluoride glasses), have poor angular acceptance of incident light and are physically thick. The optoelectronic conversion detectors, such as bulk Si photodiode or Si charged-coupled device (CCD) arrays, are challenging in the DUV region due to the very small penetration depth of UV photons. While other semiconductors, such as aluminum gallium nitride (AlGaN), are potentially superior optoelectronic converters, they are extremely challenging to manufacture and very high area cost ($/m$^2$) relative to Si. Furthermore, AlGaN is severely limited in the types of devices and manufacturing steps than can employed for mass manufacture. Therefore, without limitation to silicon or silicon-like manufacturing process, the present embodiments seek to advantageously utilize silicon-based processes where possible and complementary metal oxide semiconductor (CMOS) manufacturing processes as they provide the lowest cost and highest function per unit cost for implementing the biosensor system. Yet a further benefit of leveraging the mature Si-based nano-electronics processing technologies is the access to high throughput nanoscale lithographic patterning methods. For example, current CMOS technology nodes are patterning physical transistor features on 10 nm length scale or less. Commercial scale sub-10 nm planar lithographic patterning of materials enables new types of advanced optical devices suitable for operation in the UVC band. Furthermore, these Si-based technologies can further integrate a plurality of complex electronic functions with a single biosensor chip.

The present embodiments seek to create active biosensor chips in direct contrast to substantially passive biosensors available in the prior-art. Additionally, in the present embodiments a dispersion-free spectrometer is developed specifically for analysis of biomolecular assays and incorporated to form a biosensor. For example, a biosensing device of the present embodiments can be absent of a wavelength spatially dispersive element between a well for the analyte test sample and the detector.

This disclosure relates generally to an analyte comprising an unknown composition with the goal being to identify the number density of at least one target unknown biomolecule. That is, the goal is to quantify the presence of and, if present, the number density of at least one specific type of target biomolecule. Conventional techniques can readily prepare an assay of equivalent analyte test volumes representative of the initial unknown analyte into a test assay. For example, if the total assay volume required for the biosensor is sufficiently small, then a sample size comprising a single whole blood droplet can be used to cover an active area of the disclosed biosensor. Alternatively, an ELISA-style assay can be disposed across an active array of biosensors.

Yet a further example is a biosensor comprising a large number of specific spectral sensor arrays embedded with each analyte volume comprising the assay. This configuration enables high statistical analysis of bio-processes on a single biosensing chip. A planar optical antenna optimized for sensing and filtering optical energy in the ultraviolet range of wavelengths, may be formed using aluminum-based materials. Aluminum is a particularly advantageous material for use in the ultraviolet range of wavelengths due to the unique real and complex dielectric dispersion compared to all other CMOS compatible metals. Other metamaterials may also be utilized such metalo-dielectric and photonic bandgap materials and are claimed in their entirety herein. The substantially planar optical antenna serves as an optical filter and is disposed between the analyte under test (AUT) and the optoelectronic portion of the detector array. This proximity of the analyte with the detector greatly increases the light collection efficiency and thus the sensitivity of the device, and furthermore enables a reduced amount of analyte to be used.

Figure 4:
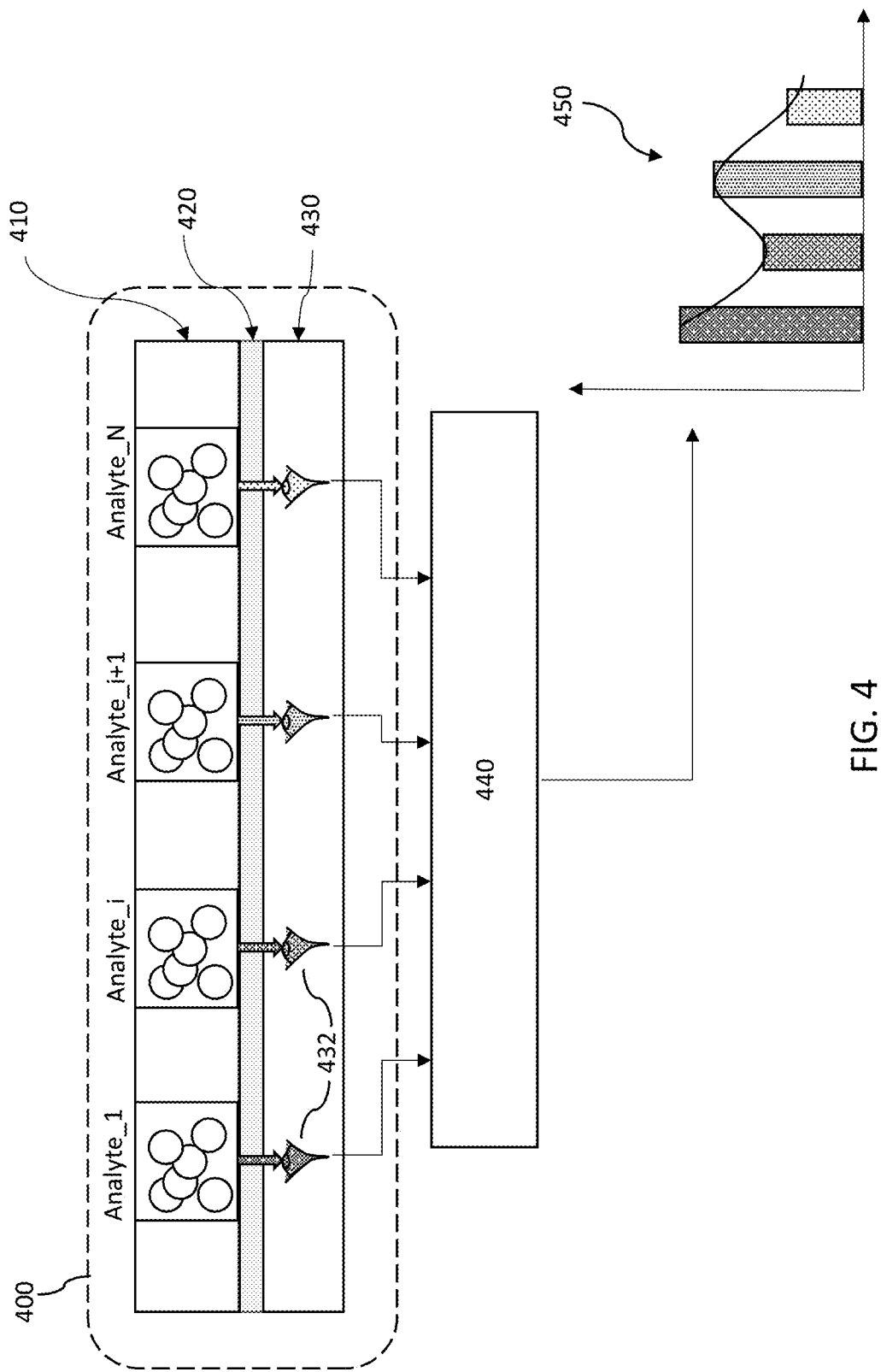
FIG. 4 is a cross-sectional schematic of a biosensing device in accordance with present embodiments.

FIG. 4 is a vertical cross-sectional schematic of the present biosensor embodiments, in which a plurality of two-dimensional (2D) planar spatially selective wavelength detector elements disposed within the detection plane enables analyte volume samples (Analyte i, where i=1 . . . N) to be disposed directly on the detector array. In the spatial optical configuration of a fluorescence excitation device shown in FIG. 4, a 2D analyte sensor 400 has a 2D analyte array 410 under test, an optical interface 420, and a 2D spatially selective wavelength detection plane 430. The close optical distance between the analytes in array 410 and the detectors in detection plane 430—i.e. where R of FIG. 3 is essentially zero in FIG. 4 (or in the range of nanometers to microns)—greatly increases the sensitivity of the device and reduces the sample size of analyte needed. No light collection optic (160, 260 of FIGS. 3A-3B) or optical dispersion component (125, 225) are needed. In FIG. 4, an analyte can be cloned or reproduced into N-samples, where the volume of each analyte sample can be on the order of nanoliters or picoliters and even femtoliters due to the high sensitivity of the device. Below the analyte volumes is the detector array which includes the optical interface 420 and the two-dimensional detection plane 430. The optical interface 420 may be, for example, silicon oxide or aluminum oxide, and may be on the order of nanometers thick. The target analyte has unique signatures in the 180-400 nm wavelength range.

As shall be described subsequently, individual detectors 432 in the detection plane 430 are each configured to detect the presence of a specific wavelength or wavelength range emitted by the analyte when irradiated with UV light. The detectors 432 comprise a simple silicon-based photodiode coupled to a new type of wavelength selective filter that serves as an optical antenna tuned to specific a wavelength. The wavelength selective filter in the 180-400 nm range is extremely challenging to manufacture using prior-art techniques, such as, conventional dielectric filters based on periodic transparent and dissimilar refractive index materials formed into a multilayer stack. Conventional fullydielectric multilayered filters typically suffer at least one of the disadvantageous properties of: (i) high absorption at the target UV wavelengths of interest and thus very lossy; (ii) require use of exotic materials such as fluoride glasses; (iii) require incompatible manufacture processes with conventional Si-based micro-electronic or CMOS manufacturing technology; (iv) require a large number of periods and thus total thickness to achieve the desired wavelength tuning or selectivity; (v) cannot be readily manufactured in planar fashion to select a plurality of filter wavelength disposed in a 2D plane; and lastly (vi) require a high cost method to manufacture.

The number of unique wavelength selective detectors 432 represents the wavelength resolution of the measured spectrum. In the present embodiments, the optical antennas (in optical interface 420) for the detectors 432 are tuned to the 180-400 nm regime, utilizing metal/dielectric antennas. In particular, aluminum provides properties that make it especially suitable to serve as an antenna material for the deep UV range.

Multiple copies of the same analyte are utilized, providing a statistically higher result. That is, multiple copies of identical analyte volumes with multiple wavelength selective detectors are provided. For example, multiple analyte volumes for a particular wavelength can be averaged, and/or multiple wavelengths can be averaged together. A signal processor 440 performs the calculations from signals received from the respective analyte volumes (Analytes i) to produce the desired output spectrum 450. For a disposable biosensor, the processing circuitry of the signal processor 440 may be provided externally to the chip as part of a module to minimize the cost of the disposable device or optimize the cost per function. For a reusable biosensor, the processing circuitry may be integrated into the chip.

Figure 5A:
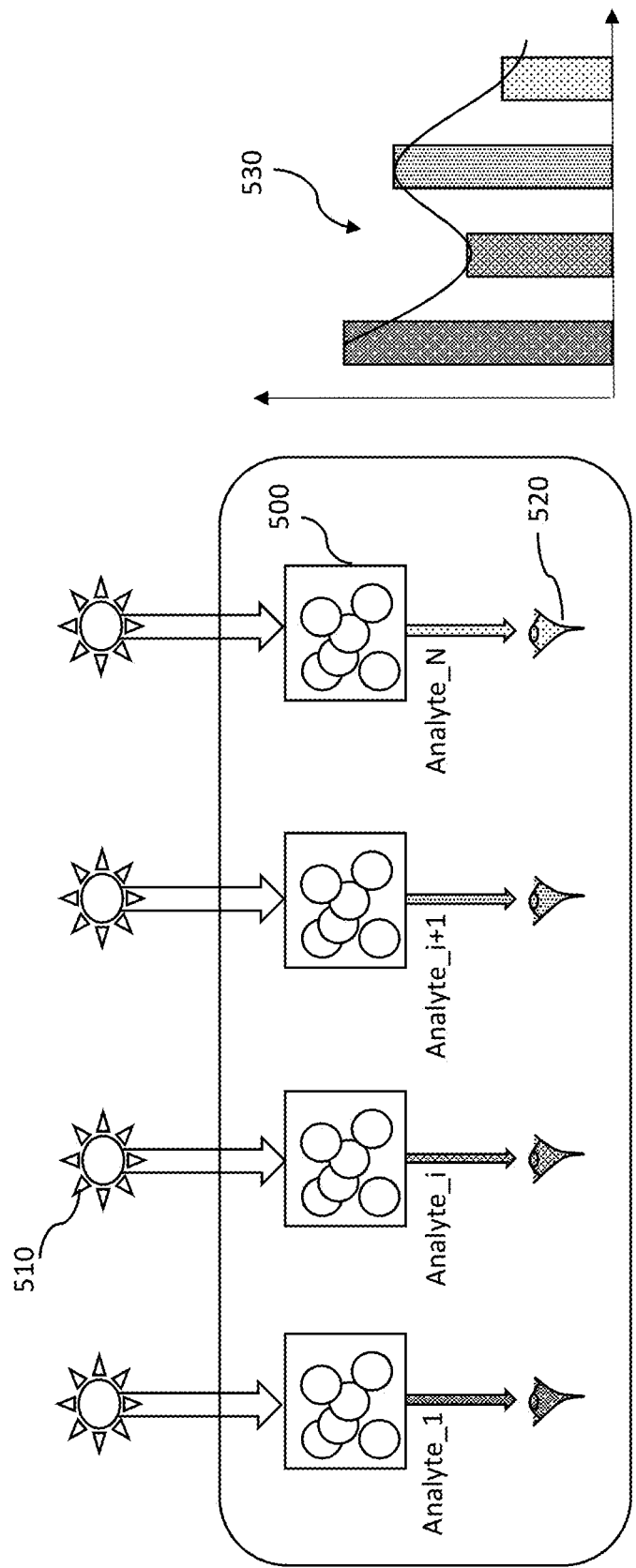
FIGS. 5A-5B show schematics of a spatial optical configuration utilizing a fluorescence excitation mode, in accordance with present embodiments.
Figure 5B:
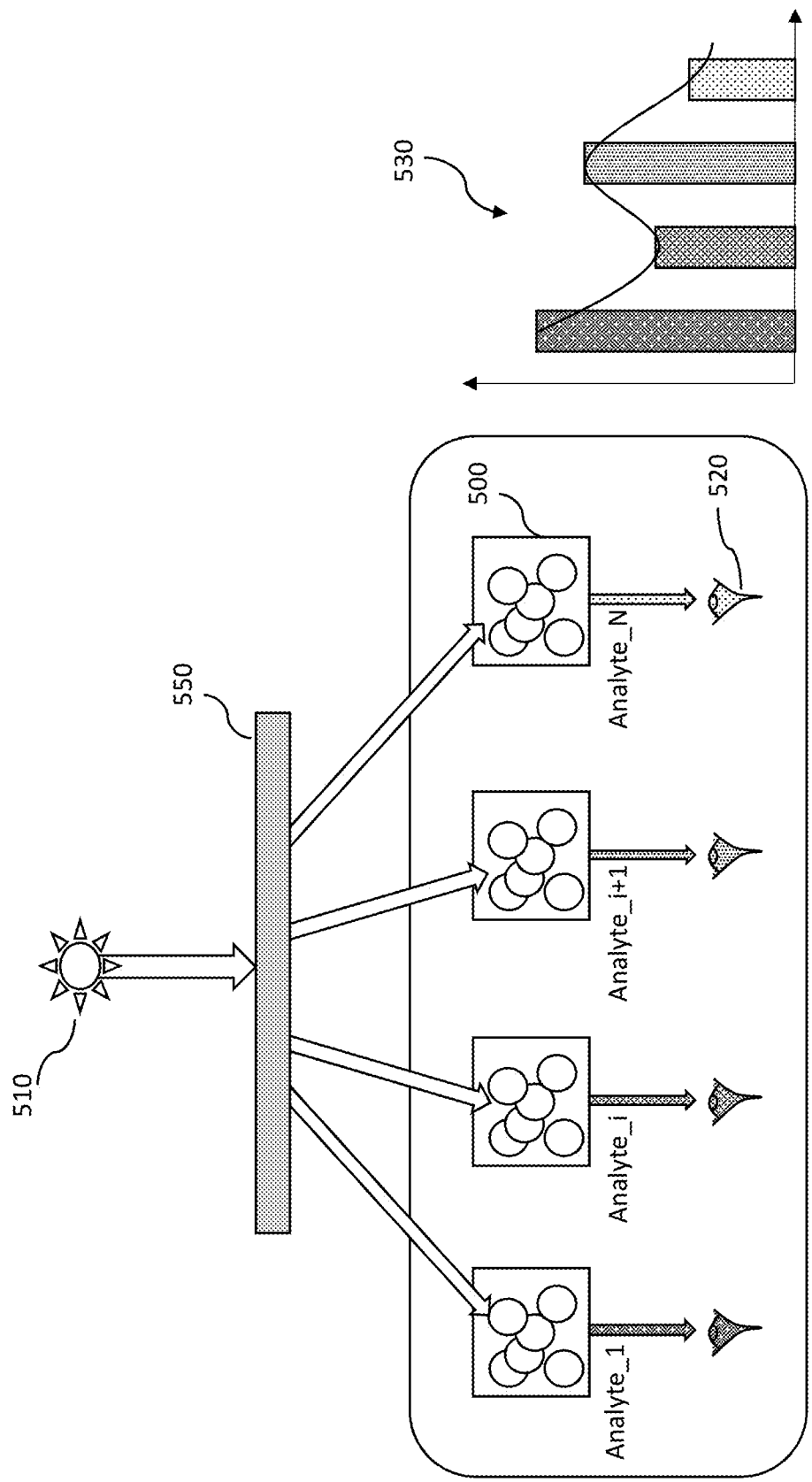

FIGS. 5A-5B show schematics of the spatial optical configuration utilizing the fluorescence excitation mode according to some embodiments. In FIG. 5A, the analyte volumes 500 (Analyte_i, where i=1 to N) are subjected to high energy excitation 510. A detector 520 tuned to a specific wavelength is disposed under each analyte 500 to measure the output response for that specific wavelength. Graph 530 shows the output responses of all the detected wavelengths. In the embodiment of FIG. 5B, the incident high energy excitation 510 can be split into a plurality of beams, for example using a holographic/diffractive optic 550, and coupled to a detector 520 as in FIG. 5A tuned to a specific wavelength which is disposed under each analyte to measure the output response for that specific wavelength. Graph 530 of FIG. 5B shows the output responses of the wavelengths detected by all the detectors 520. In both FIGS. 5A-5B, multiple copies of identical analyte volumes or predetermined titrations of the analyte with multiple wavelength selective detectors 520 are provided, resulting in statistically improved results compared to conventional sensors, while requiring reduced sample volumes. That is, a plurality of specific wavelength detection arrays can be disposed within each specific analyte volume comprising the assay. In comparison to the conventional spatial optical configurations of FIGS. 3A-3B, the spatial optical configurations of FIGS. 5A-5B according to the present embodiments show that the detectors 520 are much closer to the analyte volumes, such as directly or almost directly next to each other. This close proximity between an analyte test sample and a detector—since intermediate collection optics and wavelength dispersive components are not needed—greatly improves the measurement sensitivity compared to conventional devices.

Figure 6A:
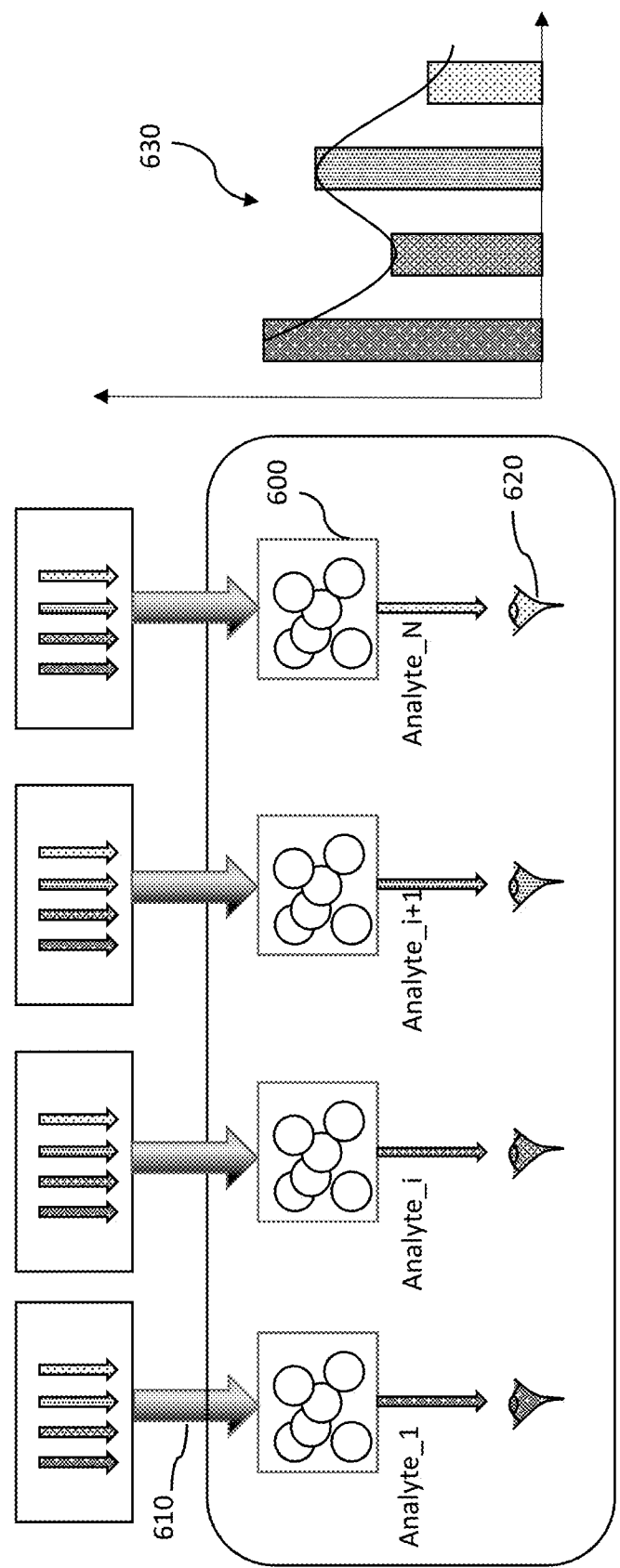
FIGS. 6A-6B show schematics of a spatial optical configuration utilizing an absorption mode, in accordance with present embodiments.
Figure 6B:
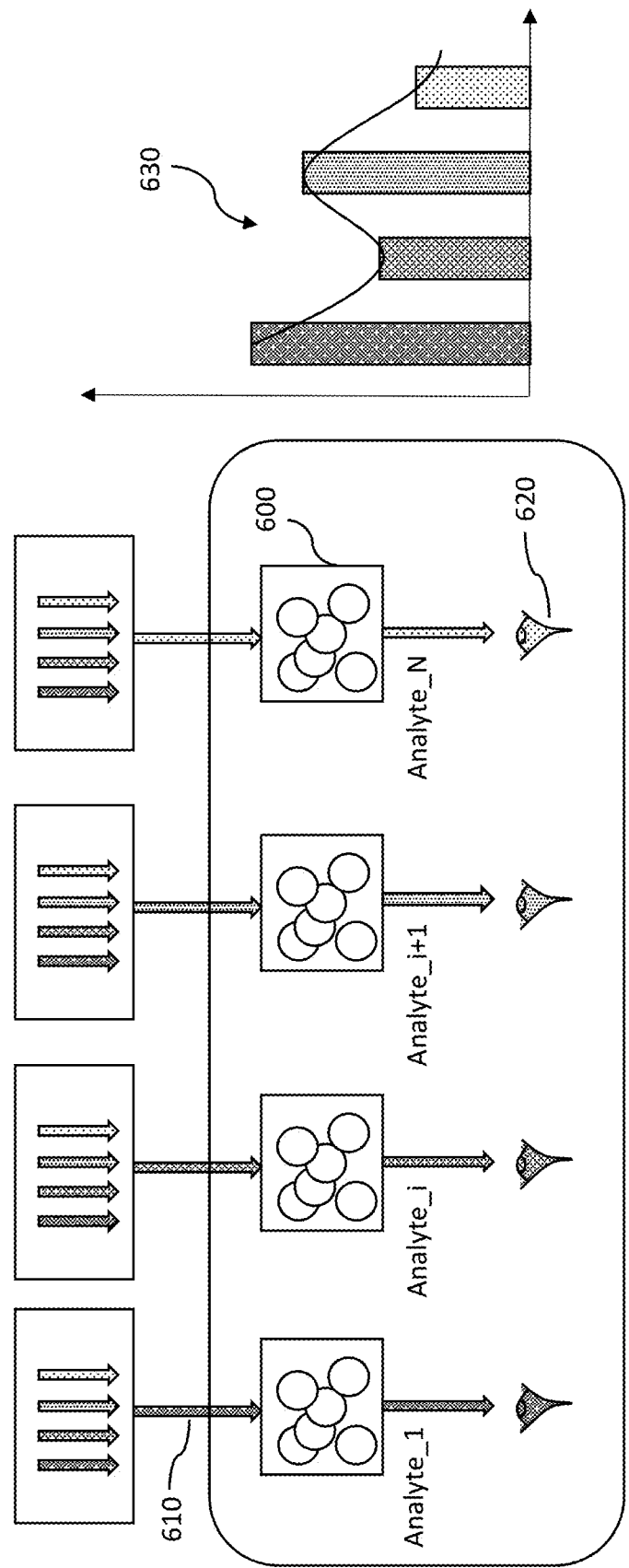

FIGS. 6A-6B show spatial optical configuration schematics of embodiments utilizing an absorption mode. In FIG. 6A an input wavelength spectrum 610 having multiple wavelengths, such as white light, is radiated onto each analyte volume 600. Each analyte volume 600 has a wavelength-specific detector 620 associated with it, to detect the output response for that particular wavelength. Graph 630 is a compilation of the output responses of the wavelengths detected by all the detectors 620. In FIG. 6B, a specific input wavelength 610 is radiated onto each analyte volume 600, and the output for each volume is detected by a detector 620 tuned to that wavelength. Graph 630 of FIG. 6B shows the wavelength responses detected by detectors 620. In both FIGS. 6A-6B, multiple copies of identical analyte volumes with multiple wavelength selective detectors are provided.

Figure 7:
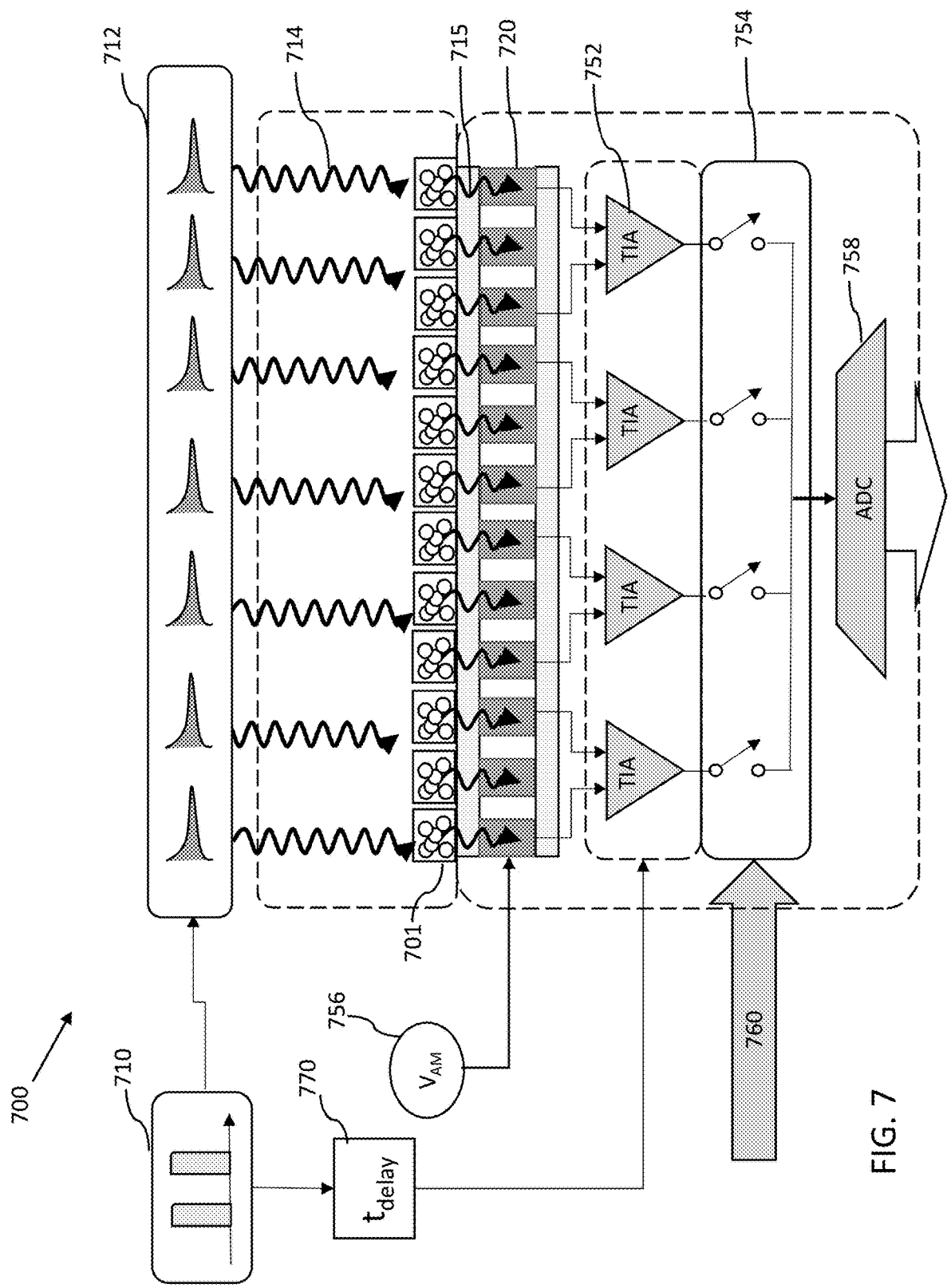
FIG. 7 is a cross-sectional schematic of an example biosensor in accordance with present embodiments.

FIG. 7 provides a more detailed schematic of a ultraviolet biosensor chip 700 in accordance with some embodiments, shown in a vertical cross-section broken out by the major functions performed. A selected analyte in a fluid (e.g., water, buffer or electrolyte) is deposited into a plurality of analyte wells 701 and is irradiated with UV radiation having a desired wavelength or band of wavelengths employing selective UV excitation 712, such as, with UVC wavelength band solid-state LEDs 710. That is, electrical excitation from LEDs 710 creates wavelength selective LED excitation 712, where the excitation energy 714 irradiates each analyte well 701. Each well 701 is configured to hold a test sample of the analyte fluid and to allow the test sample to be irradiated with ultraviolet radiation 714. The plurality of wells 701 can be of the form of open wells or be fed by microfluidic channels (not shown). Multiple analyte wells 701 are included in the device 700, into which copies of the analyte are deposited. The single analyte test substance is irradiated with UV radiation 714 of a particular wavelength, and the wavelength at which it fluoresces 715 is indicative of what the test substance might be or whether a known reaction has occurred within the reaction volume. A wavelength selective detection array 720 is located closely below the sample under test. The array 720 includes an array of spectrometers, each spectrometer tuned to be responsive to UV radiation of a desired wavelength. In other words, a plurality of detectors is configured to capture a spectral response of the test sample irradiated with the ultraviolet radiation. Each well 701 in the plurality of wells is coupled directly to a detector in the plurality of detectors, and where each detector (i.e. spectrometer) comprises a photodiode and a planar optical antenna tuned to a particular wavelength. The UV excitation fluorescence biosensor 700 of the present disclosure enables label-free detection of biomolecular materials; that is, without the need for labeling the analyte with fluorophores.

Processing circuitry is coupled to the plurality of detectors in array 720, the processing circuitry being configured to calculate an average spectral response for the plurality of detectors. In some embodiments, the target wavelengths that are averaged from the plurality of detectors is the same. In other embodiments, the target wavelengths from the plurality of detectors are different and are averaged together. In the embodiment of FIG. 7, the processing circuitry includes transimpedance amplifiers (TIA) 752 and a switch matrix 754. The transimpedance amplifiers 752 are in close proximity to the optoelectronic conversion elements (detectors 720) and serve to linearize the photocurrent generated with the incident optical power. This improves the dynamic range of the incident light that the detector can accept without saturating, and also provides good signal-to-noise for low optical power levels. The output from the array 720 is detected by the plurality of amplifiers (TIAs 752), which may provide current (e.g., $I_{ph}$) or voltage (e.g., $V_{OC}$) detection. The TIA 752 can further provide advantageous voltage or current biasing to improve the semiconductor element characteristics. For example, the TIA 752 may provide a reverse voltage bias $V_{AM}$ 756 to the silicon-based p-i-n photodiodes 720, thereby improving the temporal response and increasing the light detection sensitivity.

The switching network/matrix 754 is coupled to the amplifiers 752, and the network 754 is controlled to apply its output to an analog-to-digital converter (ADC) 758. For example, a high resolution and high dynamic range ADC 758 can be multiplexed to a plurality of detector inputs, being switched sequentially on a time scale sufficient to sample the assay with a preselected time interval. Alternatively, a plurality of ADC cores can be disposed within the electronic detector plane of the biosensor chip. The electronic representation of the process within the well is output by the ADC for a given row and column select configuration 760 that uniquely selects a given well comprising the assay. The row and select signals 760 and the downstream processing of the ADC output 758 can be provided by a secondary electronic module which may be of non-disposable type. The temporal response is desired to ascertain the time response or quantify an affinity type saturation process (namely, the chemical process) within each analyte volume. That is, if the assay is an ELISA-style titration, the temporal evolution of the assay provides an advantageous inductor for target biomolecule number density within the analyte. The output is then available for analysis.

In general, small analyte well volumes require relatively high sensitivity detection. The sensitivity of the system disclosed in FIG. 7 is further enabled by the advantageous use of synchronous excitation and detection. The well-known method of lock-in may be utilized in the present embodiments. That is, the wavelength selected excitation UV source 710 can be an LED electrically stimulated by a repetitive pulse train (shown in UV source 710 as square voltage pulses). The electrical pulse train is thus translated into a corresponding optical pulse train as a function of time and coupled to the assay. An advantageous selection or tuning of the phase delay 770 between electrical excitation signal and the synchronous detection of the detectors can be used to form a chopper stabilized or frequency locked lock-in detection system. The described synchronous detection biosensor further makes external environment noise immunity yet another advantageous feature over prior-art biosensing methods.

Figure 8:
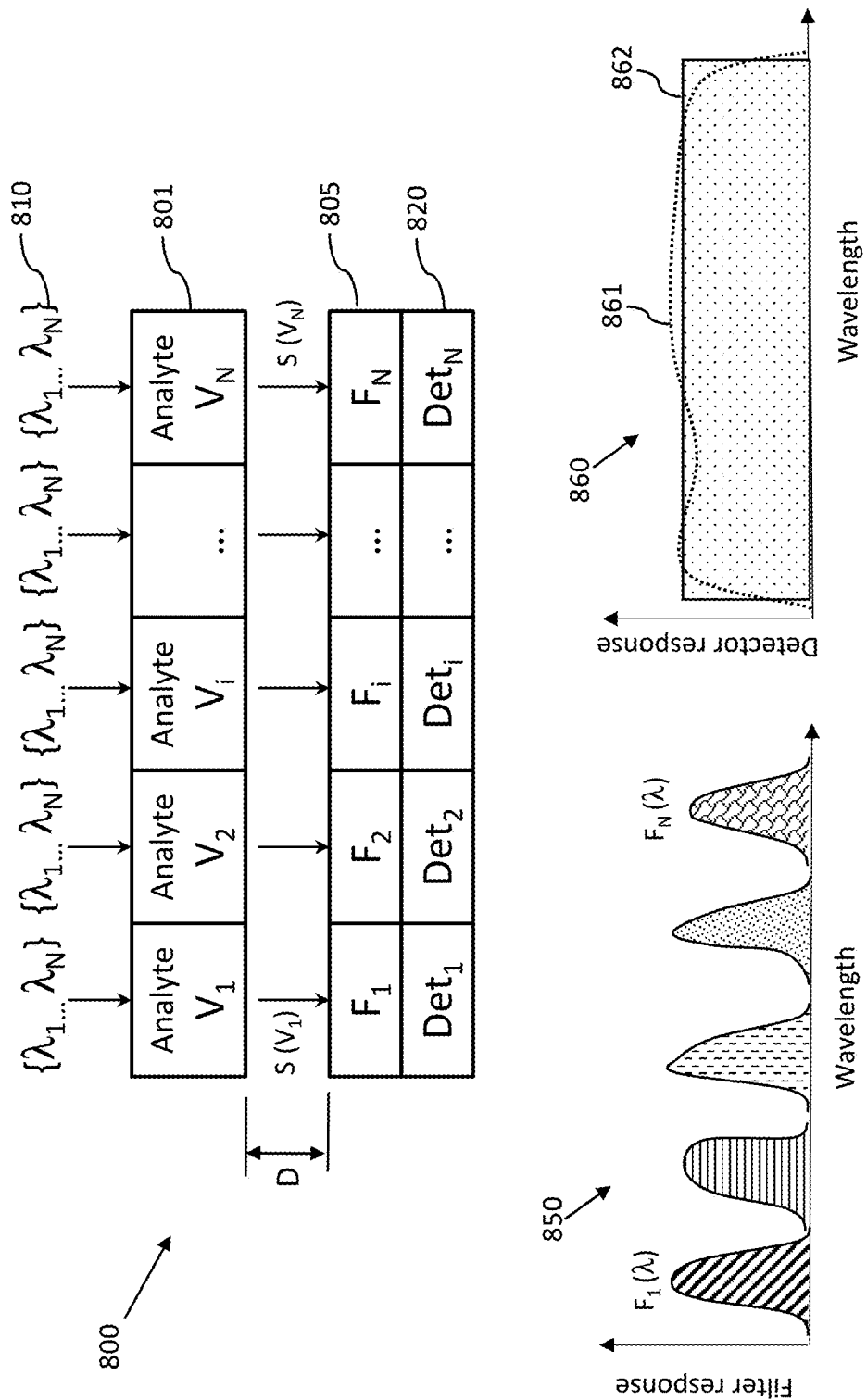
FIG. 8 provides a diagram of statistical averaging over multiple detectors.

FIG. 8 is a block diagram of how a large number N of detectors is used to evaluate the analyte. The biosensor 800 includes an array of detection units (detectors), each of which has a sample volume $V_N$ 801 with a corresponding filter $F_N$ 805 (e.g., optical antenna as shall be described subsequently) and detector $DET_N$ 820. The distance D between the analyte volume 801 and detector 820 with its filter 805 is minimal, such as zero when the volume 801 is directly on the detector 820 and filter 805. The same spectrum 810 ($\lambda = \{\lambda_1, \ldots, \lambda_N\}$) is presented to each volume 801 in this diagram. The spectral response $S(V_N)$ for each analyte volume 801 is received by each filter 805. Each filter 805 is a subtractive filter, tuned to filter a certain wavelength that can all be the same or different from each other. Graph 850 shows the response $F_N(\lambda)$ from each filter 805, which has been tuned for a particular wavelength. The biosensor 800 takes an average representation of the sample over multiple volumes as shown by graph 860, resulting in a zero dispersion planar spectrometer. Curve 861 shows the actual averaged response, which is fairly close to the ideal response shown by rectangle 862. The overall device output for each wavelength λ is more reliable since it is an average response over many samples. This averaging process occurs for each wavelength to be analyzed by the biosensor chip, where multiple sample volumes are provided for each wavelength to be detected.

The sample volumes 801, filters 805 and detectors 820 in FIG. 8 are integrated into the biosensor. This beneficially enables lower optical loss with higher sensitivity, enables the ability to have the sensor close to or immersed in the analyte, and enables a compact and planar aspect ratio. Chip arrays of $N^2$ (sensitive to M-spectral bands) are used for an overall biosensing device. In some embodiments, on-chip signal processing enables data fusion at chip level, where the well (or plurality of wells), the plurality of detectors, and the processing circuitry are integrated on a single chip. In other embodiments, the signal processing may occur off-chip. Simple sum and threshold operations can be used for optical signal processing and specie analysis.

Figure 9:
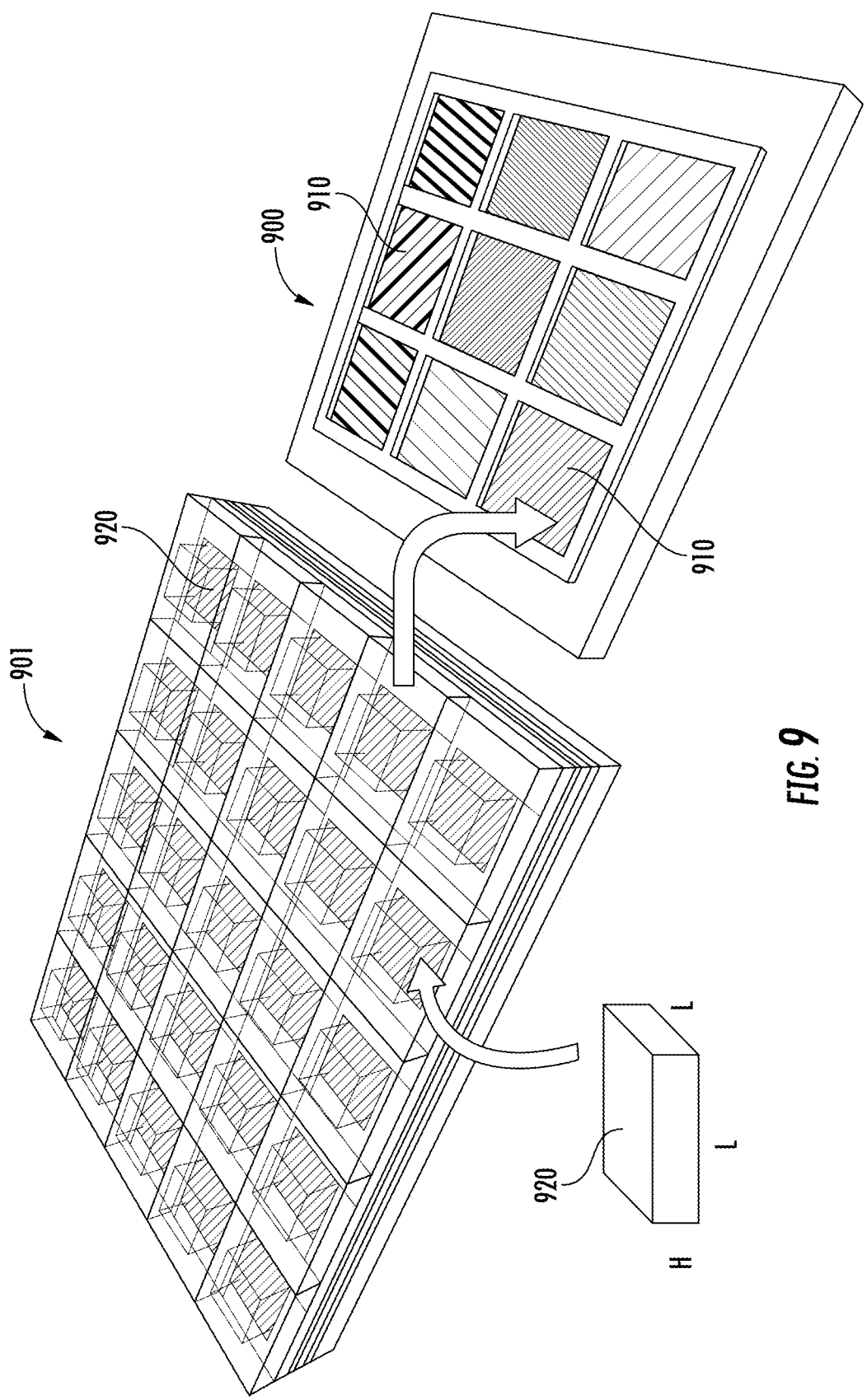
FIG. 9 shows a perspective view of a biosensor array device in accordance with some embodiments.

FIG. 9 illustrates how the spectrometers in the UV sensor may be arranged into groups for detecting various types of substances. The multiplexed macro-array biosensor 901 has twenty-five macro-pixels 920 arranged in a 5×5 array. Each macro-pixel 920 is a specific biosensing array 900 for detecting a particular substance. The same analyte is placed in a well on each macro-pixel 920 with an analyte volume of H×L×L. In the embodiment of FIG. 9, the close-up view of biosensor array 900 shows that each macro-pixel 920 is made of an array 900 of pixels 910 (e.g., a 3×3 biosensor array 900). Each pixel 910 can have multiple sub-pixels within each pixel 910, where the sub-pixels are not illustrated for clarity of the illustration. Multiple optical detectors (e.g., detectors 720 of FIG. 7) are used to form a sub-pixel, with an array of sub-pixels forming each pixel 910 that form the macro-pixels 920 of the macro-array biosensor 901.

In the embodiment of FIG. 9, a plurality of the wells 701 of FIG. 7 are grouped into the pixels 910 and macro-pixels 920 to form, for example a Y×Y biosensor assay 901. Each macro-pixel 920 may have a varying array of wavelength sensitive sub-pixels. Alternatively, each macro-pixel 920 may use a single wavelength responsive detector within it. Other embodiments may also have a combination of the desired optical pixel arrays disposed across the assay. Each macro-pixel 920 or pixel 910 may be tuned to detect a specific biomolecular process, with a specific substance optical signature, such as a protein or DNA. The biosensor array 900 (representing a macro-pixel 920) may have any number of pixels 910 determined by the complexity of the assay to be performed. Each macro-pixel 920 may have its associated spectrometers, where the spectrometers are tuned to be responsive to particular wavelengths of radiation. Thus, the multiplexed macro-array biosensor 901 of FIG. 9 can either identify nine different substances (per the different patterns shown in the 3×3 pixel biosensor array 900), or produce the wavelength resolution for a spectral signature as indicated by the different patterns in the pixels 910 of biosensor array 900. FIG. 9 also indicates the compact nature of the biosensor, where a macro-pixel volume 920 may have dimensions on the order of, for example, a height H ranging between 10 nm to 10 μm, and lateral dimensions L ranging between 1-100 μm. Pixels 920 within the biosensor array 900 may all be the same size or may have varying sizes from each other.

Figure 10:
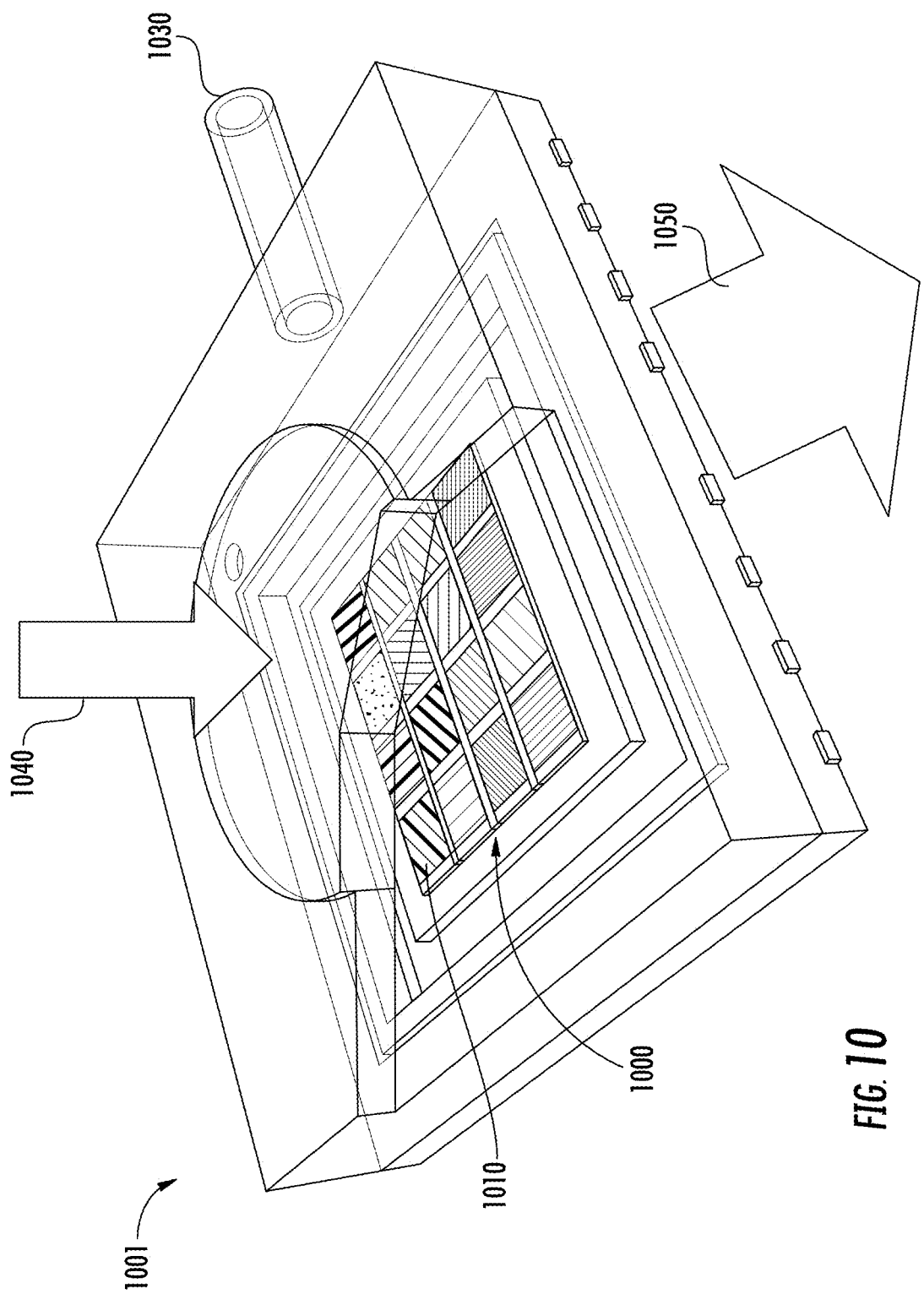
FIG. 10 is a perspective view of a biosensing system in accordance with some embodiments.

FIG. 10 shows a UV fluorescence biosensor 1000 incorporated into a high throughput system 1001. In this example, the biosensor 1000 is used to identify DNA/nucleotides, where each macro-pixel 1010 is tuned for a specific substance, as indicated by the different shading in each macro-pixel 1010 in the array. A fluid injection port 1030 allows input of the sample analyte to be tested. A broad spectrum 1040 may be input for direct absorption, or DUV excitation for fluorescence. The spectral array of biosensor 1000 may be SOT/SOS-based, or bulk silicon may be used in other embodiments. The large array size increases the statistical processing of data, where the processed spectral output 1050 provides results for the user. The fluid injection port 1030 may sequentially flow a pure and specific nucleic acid across the biosensor assay. Between each measurement involving a specific pure nucleic acid, the sensor assay volume is washed with water or buffer. Then the process is repeated. For example, the flow sequence S={A-flow/test/wash/C-flow/test/wash/G-flow/test/wash/T-flow/test/wash/} can be repeated many times for unique sequencing of attached unknown nucleic acid sequence fragments ACGT within the biosensor assay. The signal reported at each step is proportional to the amount of difference signal produced by the detector array.

Optical Antennas

Figure 11:
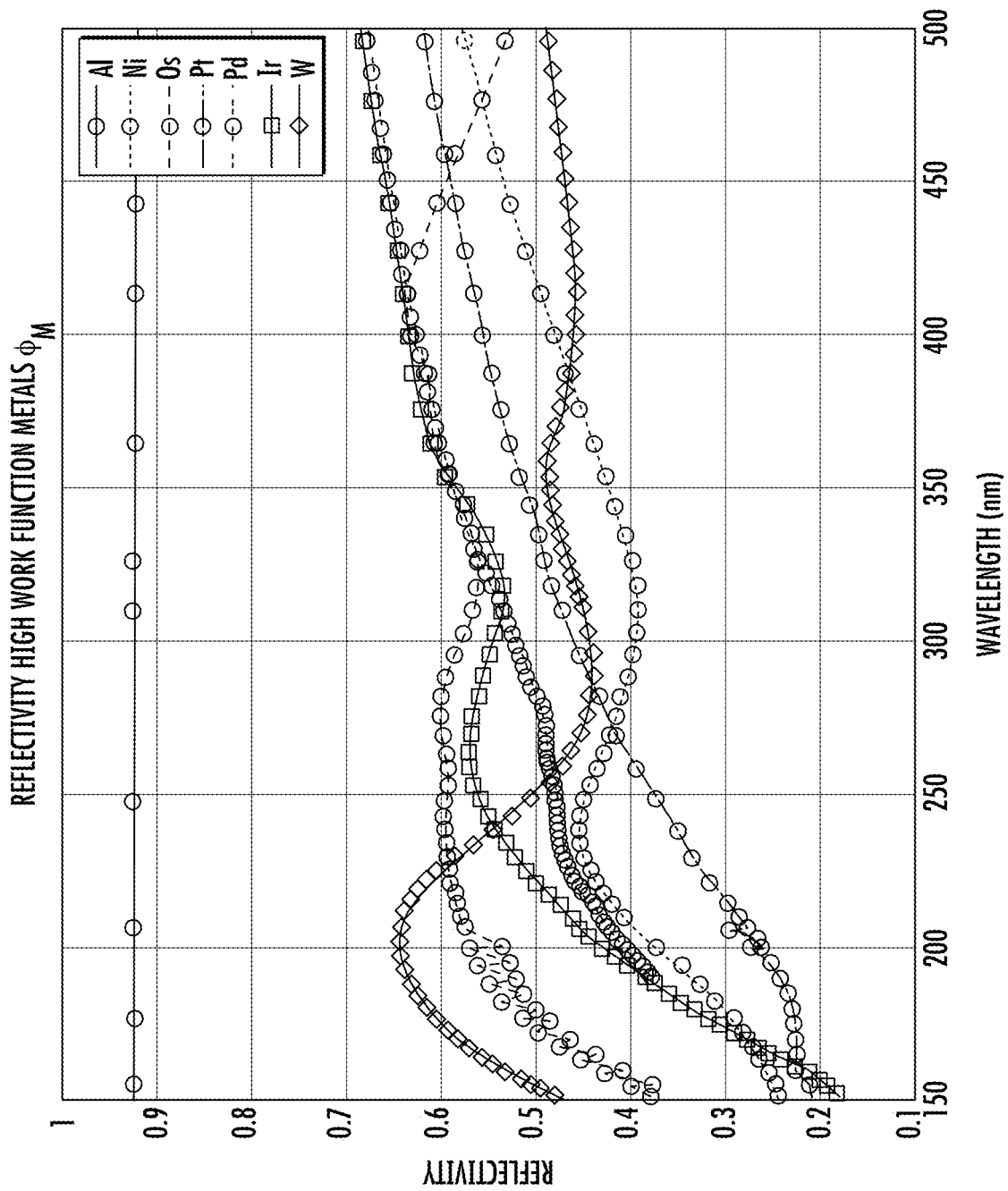
FIG. 11 is a graph of reflectivity for various metals, including aluminum, for various wavelengths.

Embodiments of optical antennas for tuning the detectors to a specified wavelength shall now be described. In various embodiments, a planar optical antenna is coupled to a photodiode and is configured to filter the spectral response from the test sample to the photodiode. The material for the planar optical antennas may be metal or a dielectric material. In some embodiments, the material is aluminum-based, such as pure aluminum, aluminum-silicide, or other aluminum-silicon alloys. Aluminum has high reflectance in the deep ultraviolet range, and is uniquely utilized in the present biosensors to serve as an optical antenna tuned to the wavelength of interest such as 180-400 nm for the deep ultraviolet range. FIG. 11 shows clearly the unique properties of Al in UV and more particularly the 180-400 nm wavelength range compared to all other common metals used in semiconductor processing.

Figures 12A, 12B:
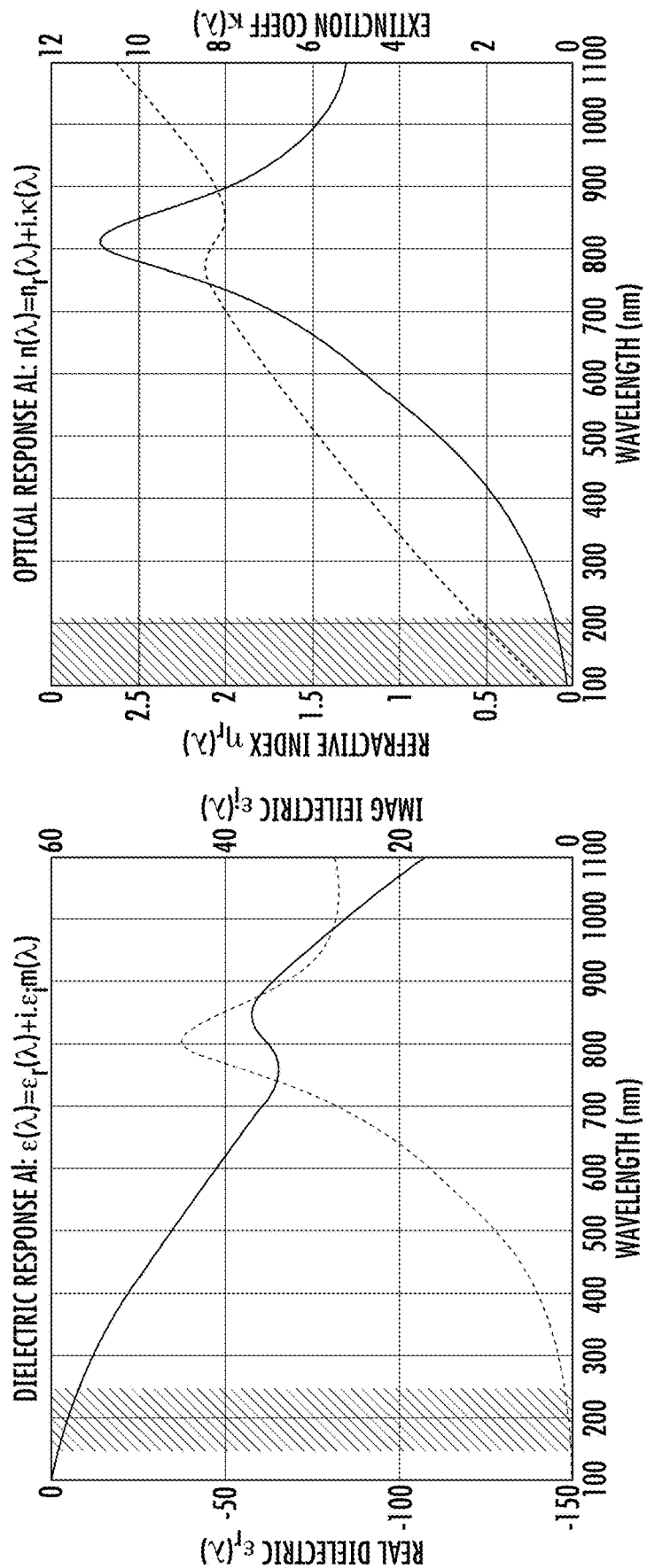
FIGS. 12A-12B are graphs of dielectric dispersion and optical dispersion for aluminum.

Referring to FIGS. 12A and 12B, the complex dielectric dispersion (FIG. 12A) and optical dispersion (FIG. 12B) are shown for Al. These properties are particularly advantageous for the formation of optical antennas due to the large difference in the real and imaginary dielectric constants in 180-400 nm range. In FIG. 12A, the real dielectric is represented by the solid line, and the imaginary dielectric is represented by the dashed line. In FIG. 12B, the refractive index is represented by the solid line, and the extinction coefficient is represented by the dashed line. The present embodiments disclose methods to construct unique resonant receiving elements in UV using spatially patterned and substantially planar metallic structures based on metals. For example, the Al properties shown in FIGS. 12A-12B may be used in a Lorentz-Drude model for finite-difference time-domain (FDTD) calculations. Various embodiments include the use of Al and Al-based metals which are compatible with CMOS manufacturing. The optical antenna forms a planar filter for the two-dimensional detector, enabling the analyte to be placed directly on the detector and achieve a high sensitivity. The antenna is designed with polarization diversity (i.e., to detect all polarizations) and with a tunable structure using planar geometry scaling.

Figure 13:
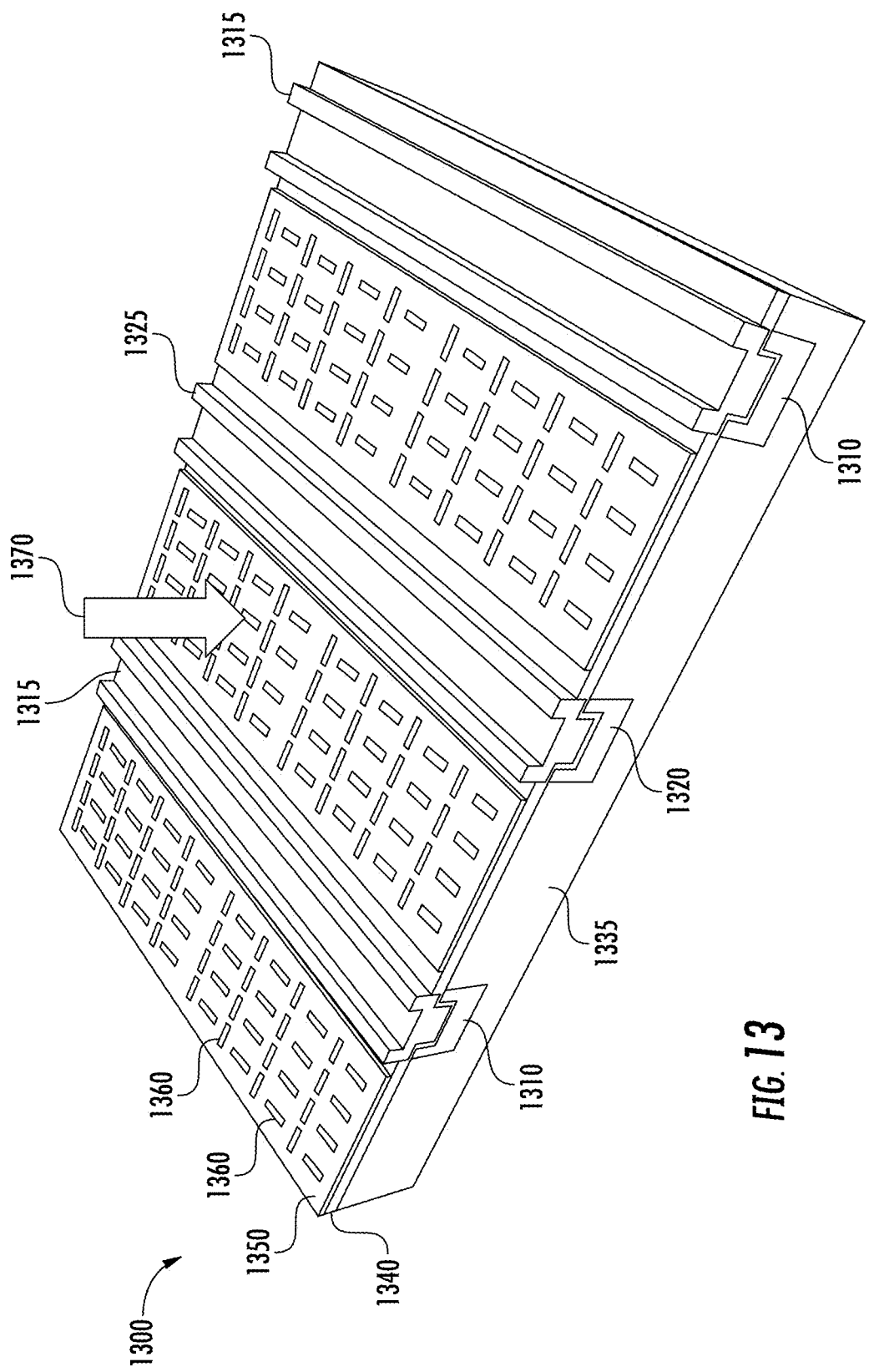
FIG. 13 is a perspective view of a portion of an example detector array having an optical antenna and an optical detector, in accordance with some embodiments.

FIG. 13 is a perspective view of a portion of an example detector array, where the portion shown is a detector having an optical antenna disposed upon an optical detector. Optical detector 1300 may be, for example, part of a 2D wavelength-selective bio sensor. The optical detector 1300 is a silicon semiconductor (though not limited to silicon) photodiode, such as a lateral p-i-n homojunction diode in this embodiment, where p-regions 1310 and n-regions 1320 are separated by the intrinsic regions 1335 (or not intentionally doped) of the silicon substrate (not shown). The detector 1300 also includes p-IDT (interdigital transducer) busbar 1315 and n-IDT busbar 1325. The silicon substrate may be bulk silicon, or may be a thin silicon-on-insulator platform. A gate oxide (GOX) layer 1340 such as silicon dioxide serves as an optical interface and dielectric between the antenna 1350 and the p-i-n detector (1310, 1320 and 1335). The planar optical antenna 1350 is coupled to the photodiode, and is configured to filter the spectral response from the test sample to the photodiode. The optical antenna 1350 in this embodiment is an aluminum plate (e.g., pure aluminum or aluminum alloy) lithographically patterned with slots 1360 in the plane of the optical antenna 1350.

The slots are configured as parallel and perpendicular slots having slot aperture geometries tuned to the wavelength of interest. For example, the length, height and width of the slots 1360 may be tuned according to the quarter wavelength of the desired wavelength to be detected. Having the slots 1360 in various orientations (e.g., parallel and perpendicular), enables various polarizations to be detected. The slots 1360 may be open or may be filled, such as filled with a dielectric or with any material that is non-absorbent to the desired wavelength. When UV light 1370 (e.g., 200-400 nm fluorescence) irradiates the surface of the detector 1300, the optical antenna 1350 filters the radiation such that only the target wavelength passes through. The radiation passing through the filter (i.e., optical antenna) creates a current in the underlying diode, and the amount of current can then be correlated to the amount of radiation.

The detector section shown in FIG. 13 may correspond to one or more analyte volumes. For example, one analyte well (ref. FIG. 7) may have multiple p-i-n photodiodes under each well. The p-i-n diode may be formed by a plurality of interdigitated electrodes with the optical antenna patterned between the electrodes. The detectors are highly sensitive due to the close proximity of the detectors to the analyte, and therefore only a small amount of analyte is needed. For example, the analyte sample may be on the order of picoliters or nanoliters or even femtoliters. In some embodiments, all the antennas of that analyte well are tuned for the same wavelength, so that the responses of all the detectors of that analyte well are averaged together. In other embodiments, each well may correspond to one p-i-n photodiode. Multiple analyte wells may be combined into a sub-pixel of an overall biosensing device. Different analyte wells, such as in different pixels of the biosensor, may be tuned for different wavelengths according to the substance to be identified. In some embodiments, a plurality of wells and a plurality of detectors are grouped into a first set of detectors in a first pixel of a biosensor, and second set of detectors in a second pixel of the biosensor. The planar optical antennas of the first set of detectors in the first pixel are tuned to a first wavelength. The planar optical antennas of the second set of detectors in the second pixel are tuned to a second wavelength different from the first wavelength.

Figure 14:
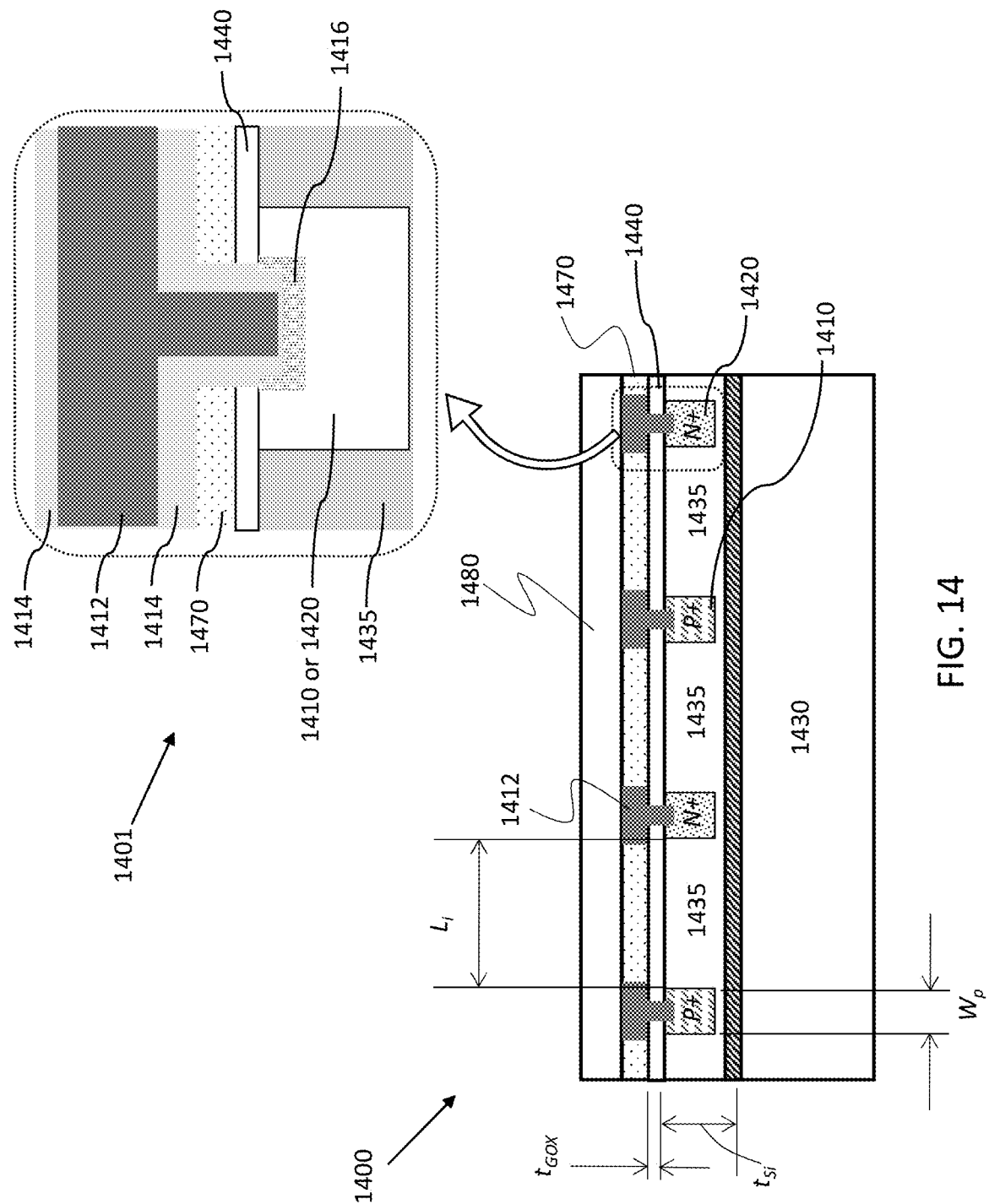
FIG. 14 shows a cross-section of an example silicon-on-sapphire detector in accordance with some embodiments.

FIG. 14 shows vertical cross-sectional schematics of an example of a thin-film silicon-on-insulator (SOI) or silicon-on-sapphire (SOS) DUV detector 1400 with a lateral p-i-n diode configuration, demonstrating Si CMOS optical to electronic conversion. SOI and SOS are capable of wavelength detection in the DUV range by virtue of the short penetration depth of UV photons in the thin film Si, providing opportunity for high responsivity and wavelength selectivity. The CMOS compatible formation process is shown in the lower schematic of detector 1400 in FIG. 14 which illustrates an overview of the SOS platform, and the upper schematic 1401 provides a more detailed view of the electrode (metal #1) via area. The optical p-i-n detectors are provided on a sapphire substrate 1430 (e.g., sapphire R-plane), where the p-i-n detectors include a non-intentionally doped (NID) silicon 1435 with p-doped regions 1410 and n-doped regions 1420. P-doped regions 1410 and n-doped regions 1420 are made of implanted silicon. Aluminum serves as metal #1 and the via material 1412 for the doped regions 1410 and 1420, where the aluminum via 1412 is coated with titanium nitride (TiN$_X$) 1414 in this embodiment, and titanium silicon (TiSi$_X$) 1416 at the interface with the doped region 1410 or 1420. The detector 1400 also includes gate oxide (GOX) layer 1440 having a thickness $t_{GOX}$ and non-doped silicate glass (NSG) layer 1470. The active layer of crystalline silicon 1435 has a thickness of $t_{Si}$, the lateral p-i-n diode intrinsic region has a width $L_i$ and the implanted p-type and n-type regions 1410 and 1420 have a width Wp. The optical antenna is formed either upon the insulating silicon nitride (SiN$_X$) layer 1480 or as part of the Metal #1 (1412) formation process.

Lithographic patterning is an efficient method to construct the planar optical antennas of the present devices. The optical filter/antenna provides spatially selective wavelength responses beneath each analyte region and is what makes the biosensor a 2D spectrometer (non-dispersive). The optical antennas are tuned using geometric elements which shall be described below. In various embodiments, the planar optical antenna comprises a structure or a plurality of structures having dimensions configured to tune the planar optical antenna to the particular wavelength. In some embodiments the structures are apertures, where the apertures are chosen from the group consisting of: single slots, grouped slots, and patches. The apertures are tuned to the desired wavelength using dimensions of the apertures, where the dimensions can include length, width, height, and spacing between the apertures. In other embodiments, the structures are pillars, where the pillars can be, for example, monopole or dipole antennas. The pillar-type antennas are tuned using dimensions including the height, width, spacing between the pillars, and vertical cross-sectional shapes of the pillars. The planar optical antenna may be configured for polarization insensitivity by tailoring the positioning of the plurality of structures. That is, the plurality of structures may have a positional arrangement configured for polarization insensitivity. For example, the structures may include a plurality of slots, where the positioning for polarization insensitivity comprises a first group of the plurality of slots being orthogonal to a second group of the plurality of slots as shown in FIG. 13.

Figure 15A:
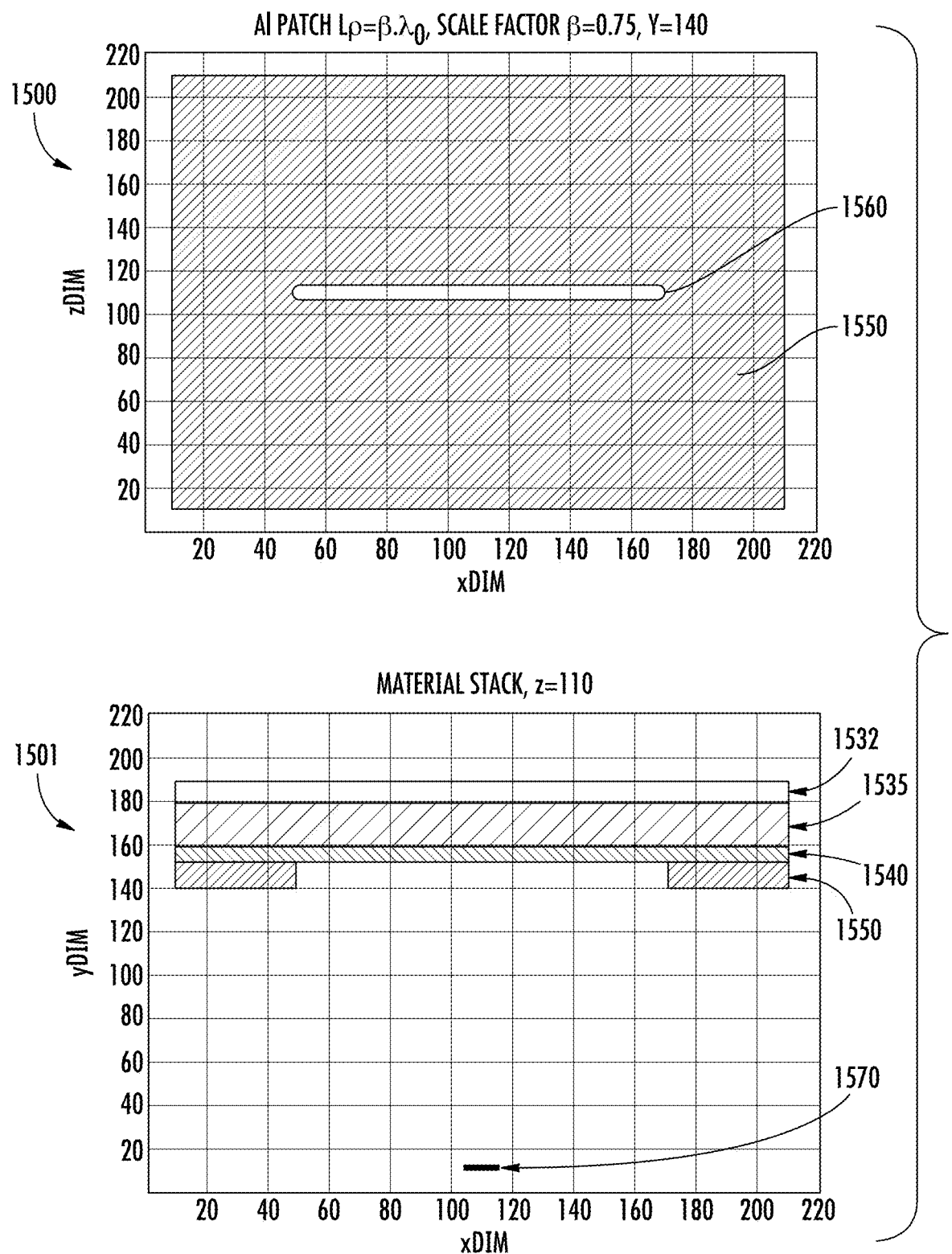
FIGS. 15A-15E illustrate a single slot type of optical antenna in accordance with some embodiments.
Figure 15B:
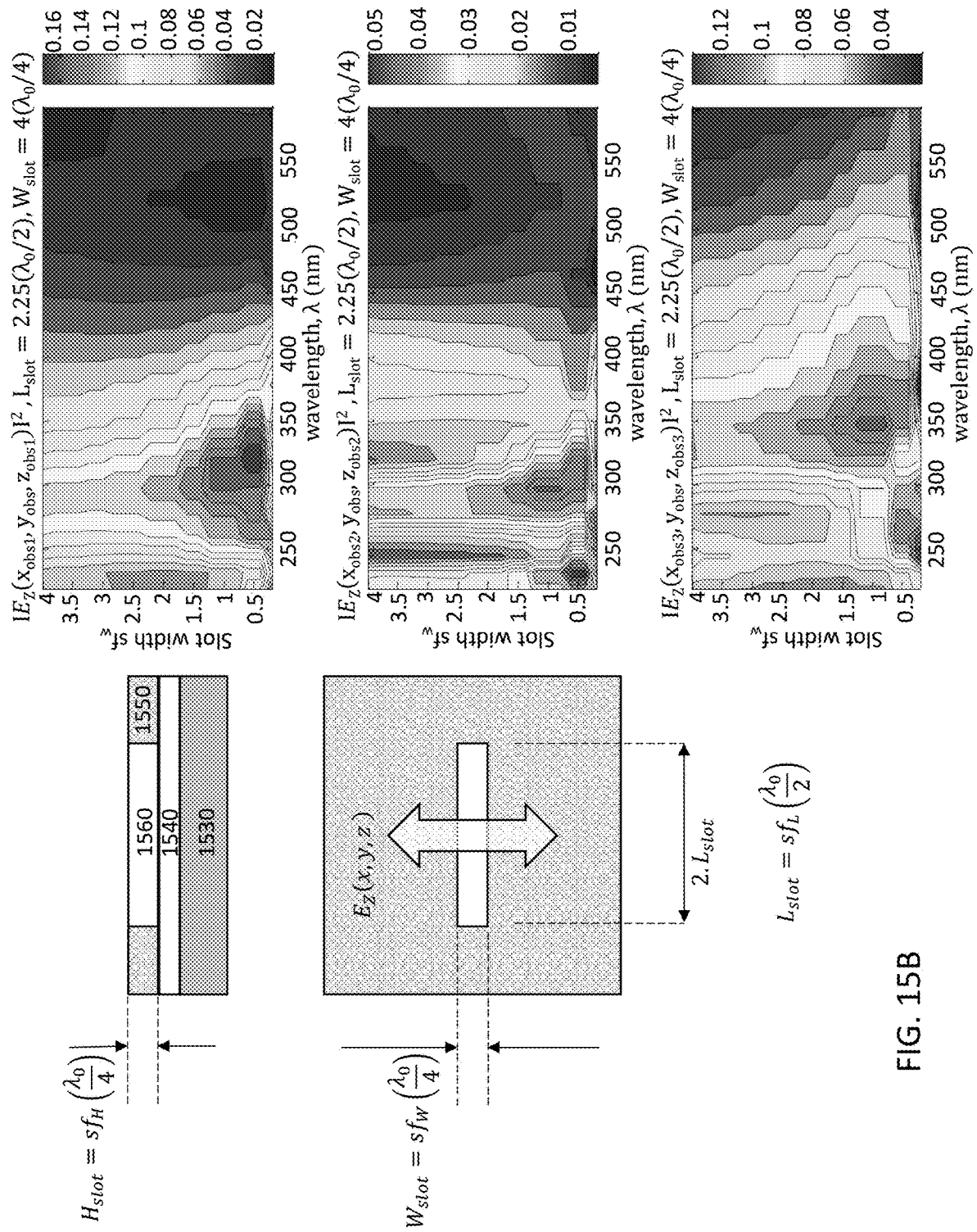
Figure 15C:
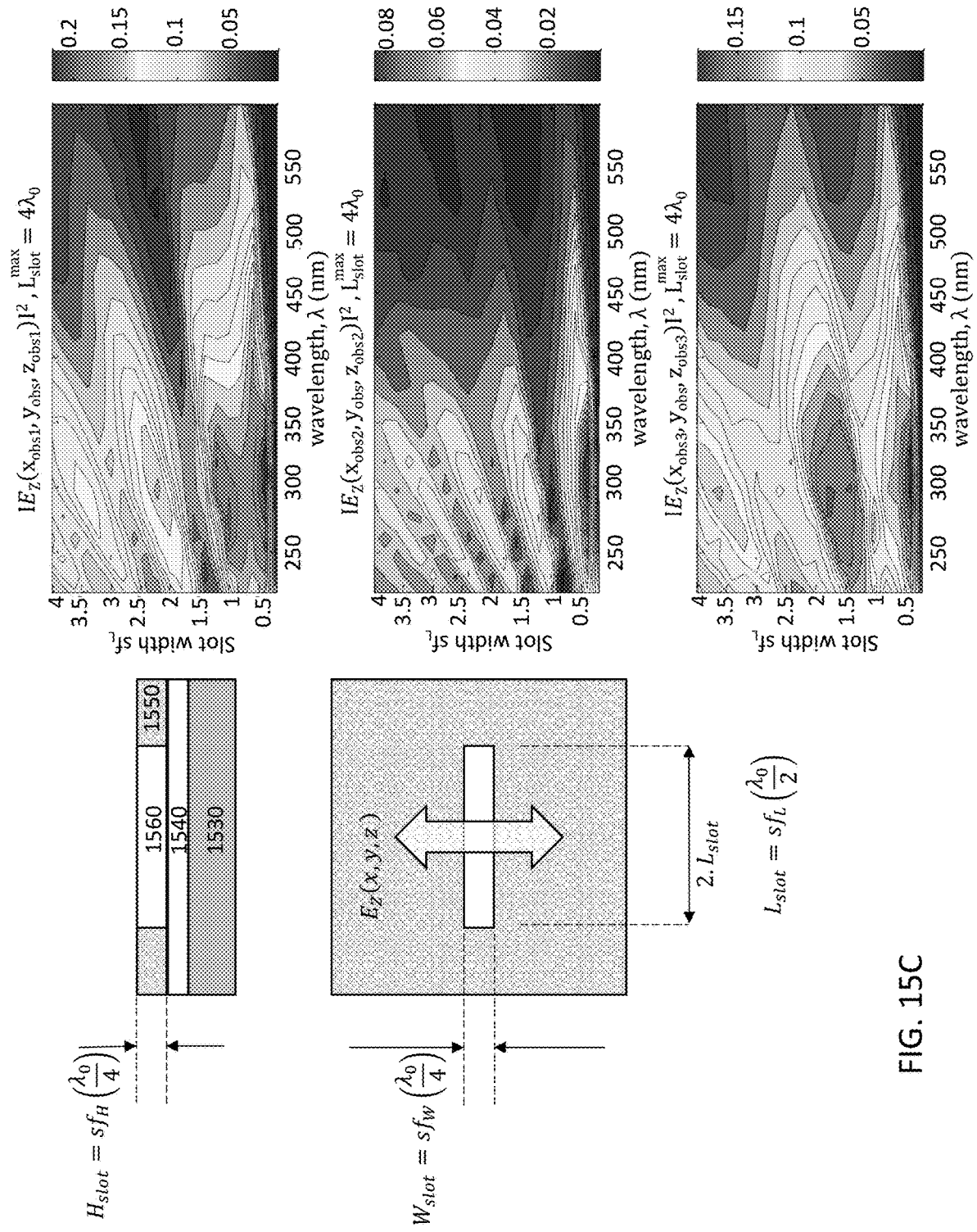
Figure 15D:
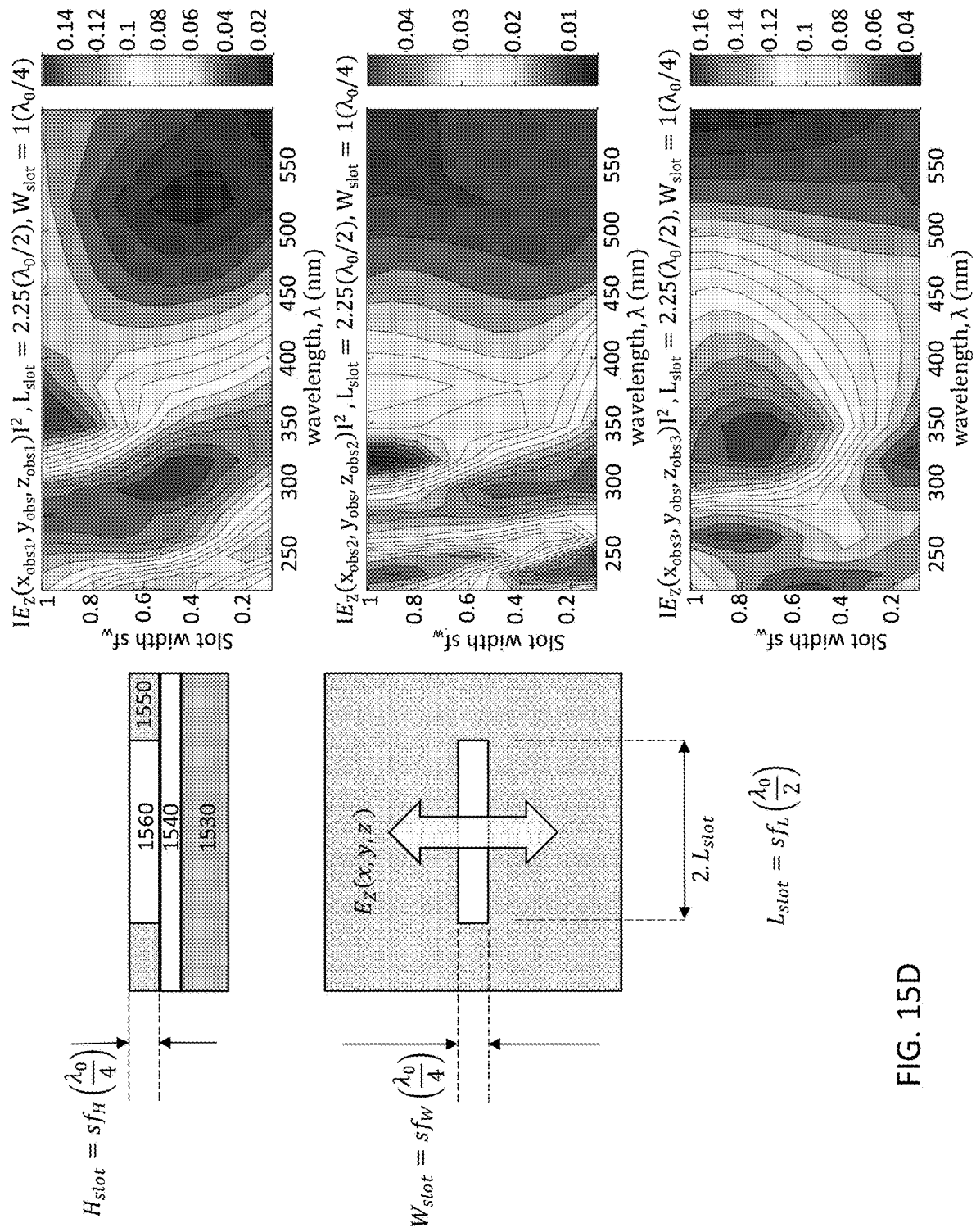
Figure 15E:
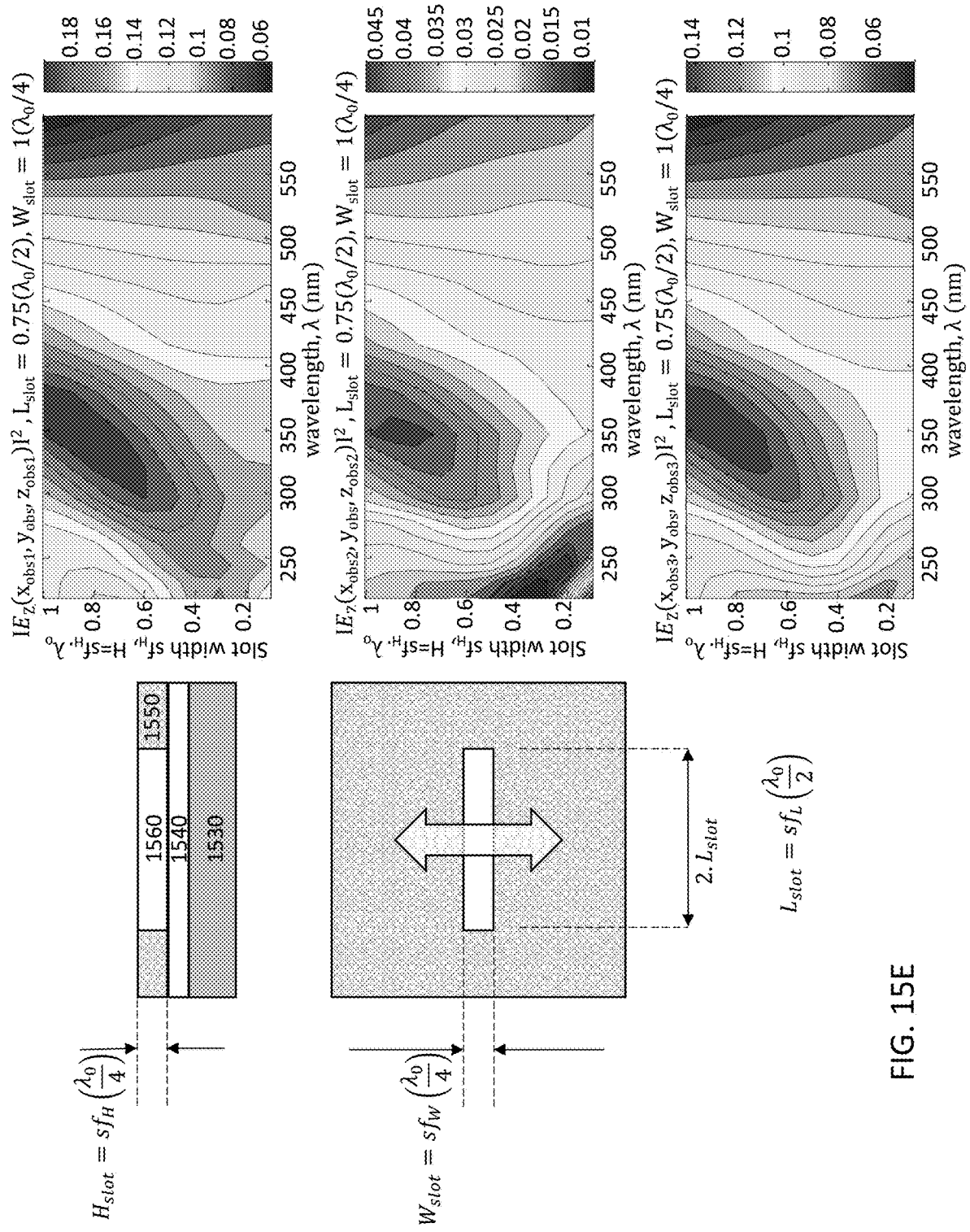

FIGS. 15A-15E illustrate a single slot type of optical patch UV antenna. The linear slot design is simulated for an aluminum plate, where in FIG. 15A a plan view 1500 and cross-sectional material stack 1501 are shown for a UV antenna 1550. Radiation emanates from the UV source 1570 and passes through the optical slot 1560 of UV antenna 1550. The UV antenna 1550 is mounted on a gate oxide layer (GOX) 1540, which is on fully-depleted silicon active layer 1535, which is on buried oxide layer (BOX) 1532. Gate oxide layer 1540 may include, for example, SiO$_2$ and AlN. FIGS. 15B-15E demonstrate simulation scenarios to tune the width, length, and height (slab thickness) dimensions of the slot 1560 for achieving the desired wavelength filtering. FIG. 15B demonstrates antenna air slot width (Wslot) tuning; FIG. 15C demonstrates antenna air slot length (Lslot) tuning; FIG. 15D demonstrates antenna aluminum slab thickness (Hslot) tuning; and FIG. 15E demonstrates aluminum slab thickness tuning of the resonant air slot, where the UV wavelength λ=300 nm. The 2D mapping graphs in FIGS. 15B-15E represent the magnitude of the detected optical emission within the Si layer sampled at different positions within the slot, namely, edge (top graph), mid-center (second graph), and center of the slot (bottom graph). The parameter space disclosed is for slot width factor sf$_W$ which is a multiple of the design quarter wavelength λ$_0$. By way of example, the wavelength response for different values of slot width or length is disclosed showing wavelength selectivity achievable. It is desired to set the slot dimensions for highest transmission/absorption into the silicon (or semiconductor if not Si-based) active layer for the specific wavelength to be detected. Thus, each detector may be configured with a specific slot design according to the particular wavelength for which the detector is to be operated.

Figure 16:
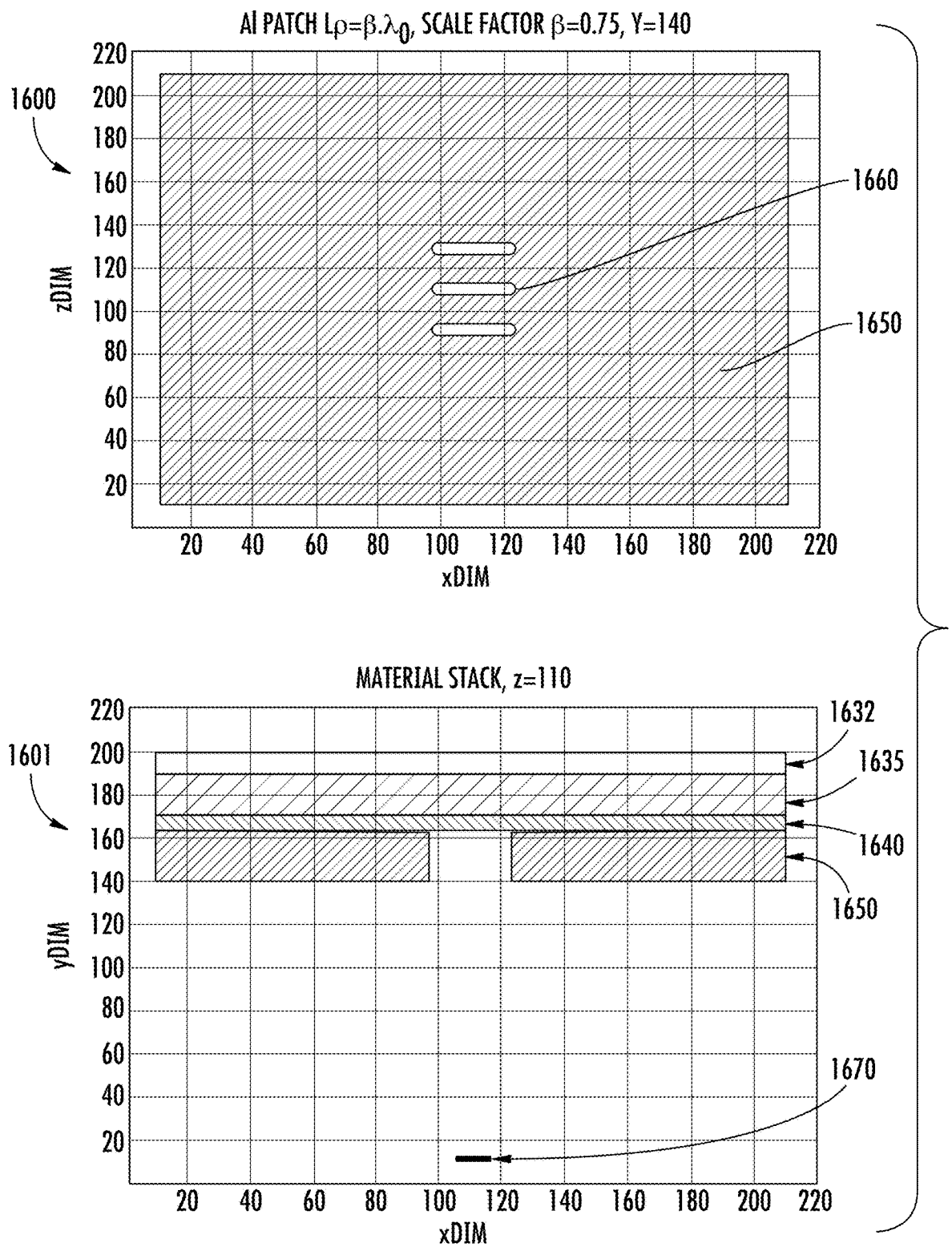
FIG. 16 illustrates a grouped slot geometry of an optical antenna in accordance with some embodiments.

FIG. 16 shows an embodiment of an antenna using grouped slots, embodied as a triple coupled slot geometry in an Al plate. Plan view 1600 and cross-sectional material stack 1601 are shown for UV antenna 1650. Similar to the device of FIG. 15, the device of FIG. 16 has a buried oxide layer 1632, a fully-depleted silicon active layer 1635 on the BOX layer 1632, a gate oxide layer 1640 on the Si layer 1635, and a UV antenna 1650 on the GOX layer 1640. The antenna 1650 has three linear slots 1660 through which radiation from UV source 1670 passes. By way of example, the triple coupled slot geometry—resembling a Yagi-Uda type antenna—can be constructed in the optical domain in the present embodiments. The multi-slot optical antenna is polarization sensitive consisting of multiple parallel elements in a line and are usually half-wave dipoles. To improve the polarization diversity of the Yagi-Uda slot antenna a plurality of oriented slot triplets can be positioned at a plurality of angles in the plane. The slots are air slots, resulting in a resonant optical antenna. The slot dimensions as well as the spacing between slots can be optimized to tune the antenna for a specific wavelength.

Figure 17A:
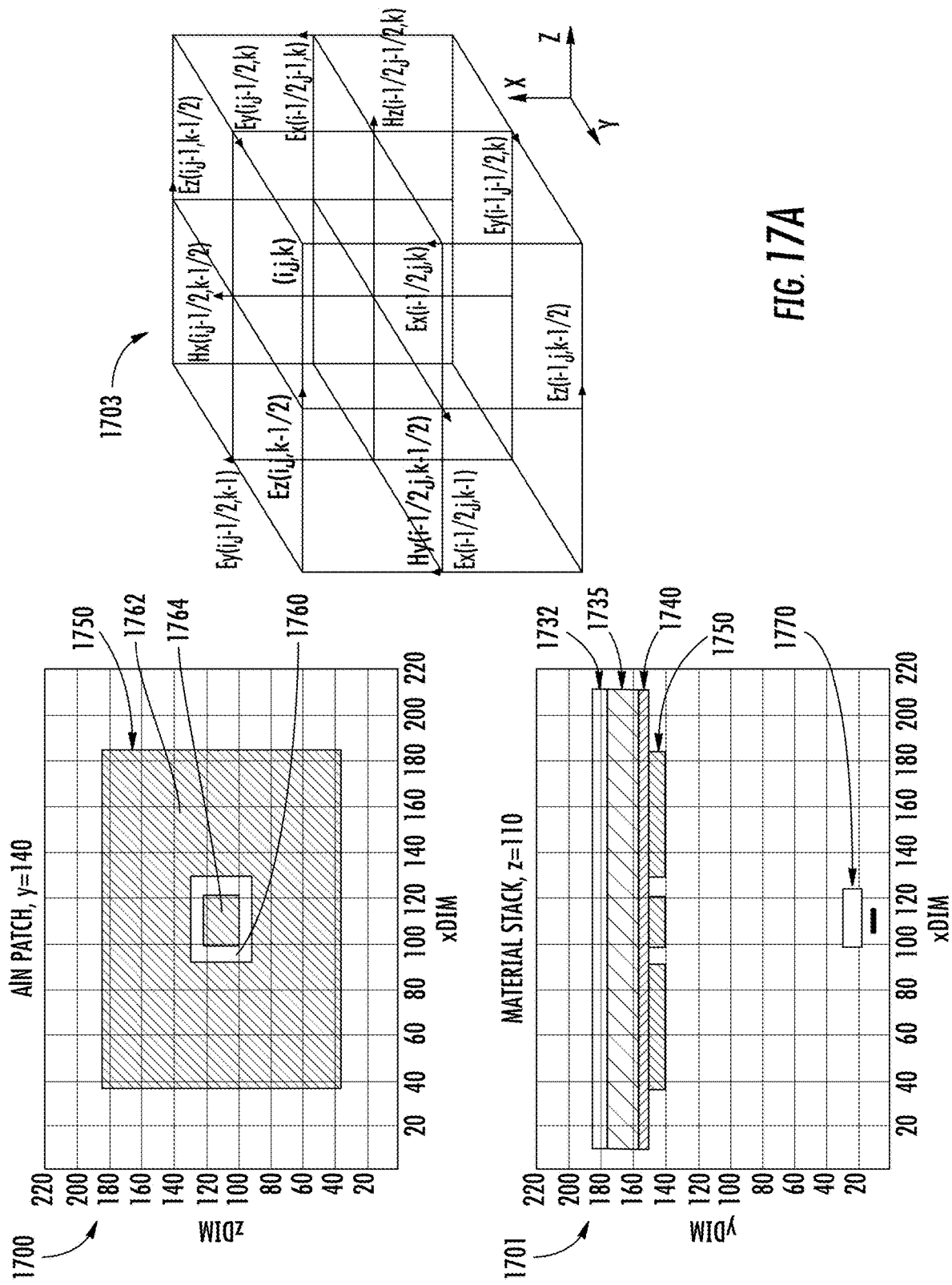
FIGS. 17A-17C illustrate a slot/patch type of optical antenna in accordance with some embodiments.
Figure 17B:
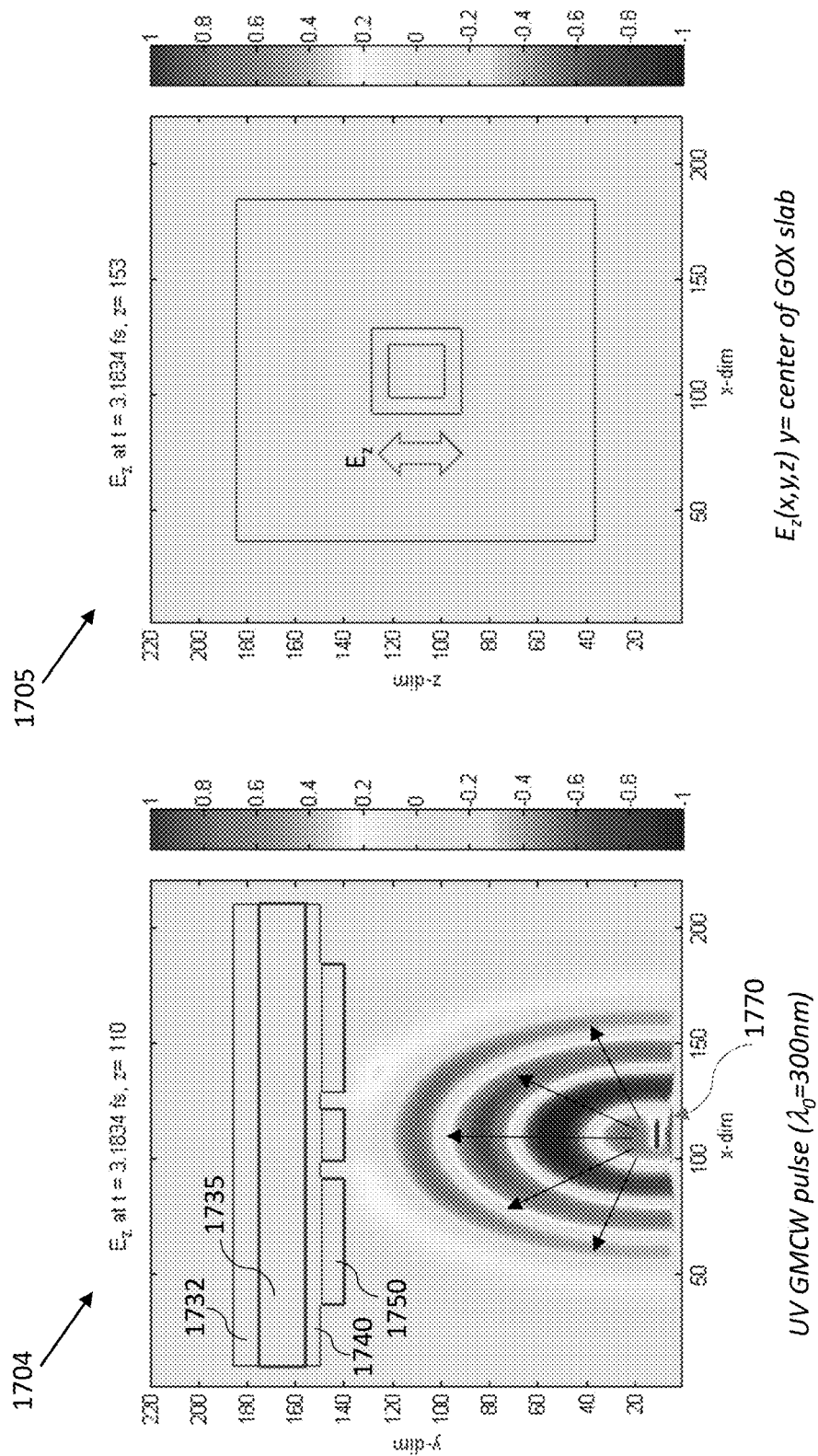
Figure 17C:
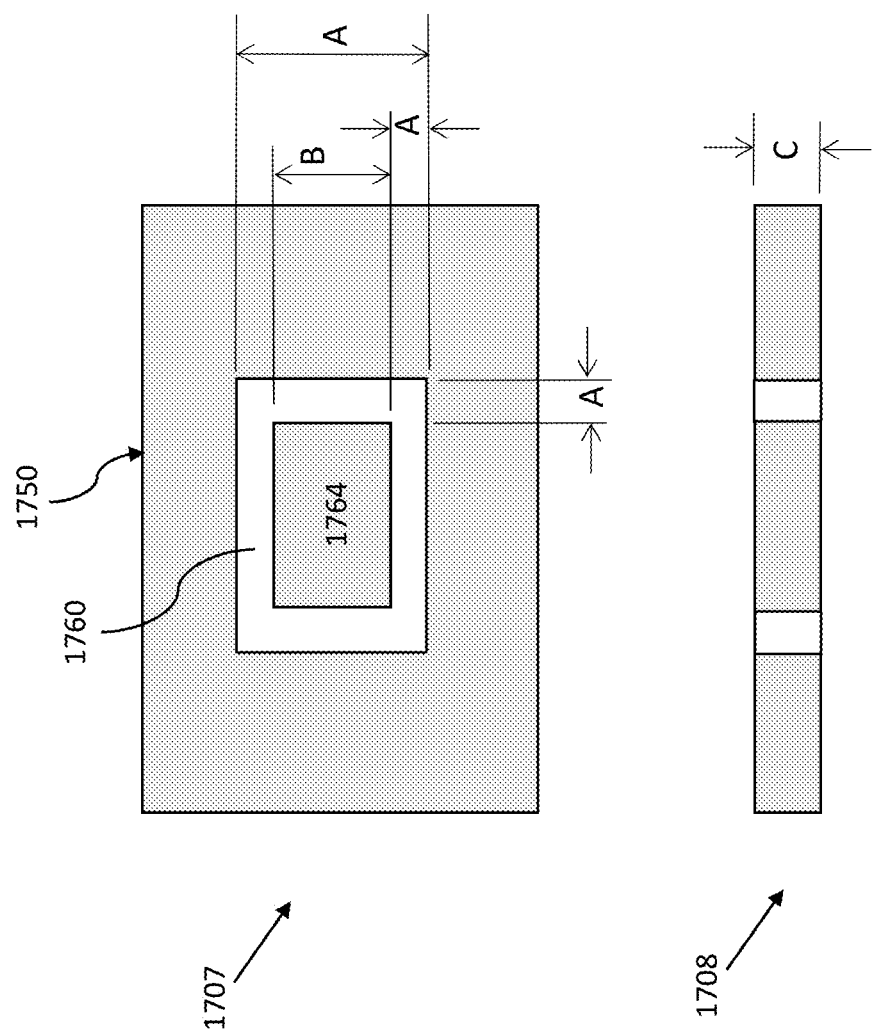

FIGS. 17A-17C show embodiments of an optical patch slot geometry in an aluminum plate, where an aperture outlines a rectangular annulus patch. Plan view 1700 and cross-sectional material stack 1701 are shown. The device of FIG. 17 has a buried oxide layer 1732, a fully-depleted silicon active layer 1735, a gate oxide layer 1740, and a UV antenna 1750. Radiation is emitted from UV Gaussian modulated continuous wave (GMCW) region 1770. The antenna 1750 is made of aluminum and has a rectangular annulus slot 1760 that serves as a vertical and horizontal antenna. The slot 1760 is bounded by a ground plane 1762 forming the outer border of the slot 1760, and an interior patch antenna 1764 forming the inner border of the slot 1760. Wavelength response to the antenna can be simulated using, for example, finite-difference time-domain methods. Model 1703 shows displacement of the electric and magnetic field vector components about a cubic unit cell of the Yee space lattice. In an example of a custom three-dimensional FDTD Matlab code used in simulations, the number of Yee cells was $(220)^3$, the FDTD computation time was 3 hours (4 core, 3 GHz), 3 ports were used for observation fields, the UV input pulse was a GMCW, and the center wavelength GMCW UV pulse was λ$_0$=300 nm.

FIG. 17B illustrates an example simulation, representing a snapshot of a UV pulse source 1770 interacting with the patch slot type of bio-sensor of FIG. 17A. The graded intensities indicate the magnetic-dipole response to incident Ez(t). The left-hand diagram 1704 is a vertical cross-sectional view of the response from a UV Gaussian modulated continuous wave at a specific time point. The UV pulse represents a biomolecular emitting a fluorescence pulse comprising a range of wavelengths. The optical pulse interacts with the optical patch antenna formed on the Si detector. The right-hand diagram 1705 is a plan view of emission at the center of the GOX slab as a result of the slot/patch for the case of the polarization shown.

FIG. 17C shows further description of a general patch design for an aluminum resonant filter 1750, having a patch 1764 surrounded by a slot 1760. The slot 1760 serves as a channel that is filled with a suitable dielectric material of dimensions selected for the wavelength λ being detected. In some embodiments, the dielectric is air. Shapes other than square/rectangular for polarizing the incident radiation may be used. View 1707 is a plan view, and view 1708 is a vertical cross-sectional view. In the embodiment of FIG. 17C, the patch thickness (height) "C" is ¾ $\lambda/n_{gap}$, the channel gap "A" is ¾ λ, and the outer dimension of the square patch "B" is ½ $\lambda/n_{gap}$, where $n_{gap}$ is the refractive index of the gap. The planar geometrical dimensions A, B and C can be varied, such as by lithographic patterning for creating the filter (antenna) 1750, to tune the wavelength response.

Figure 18:
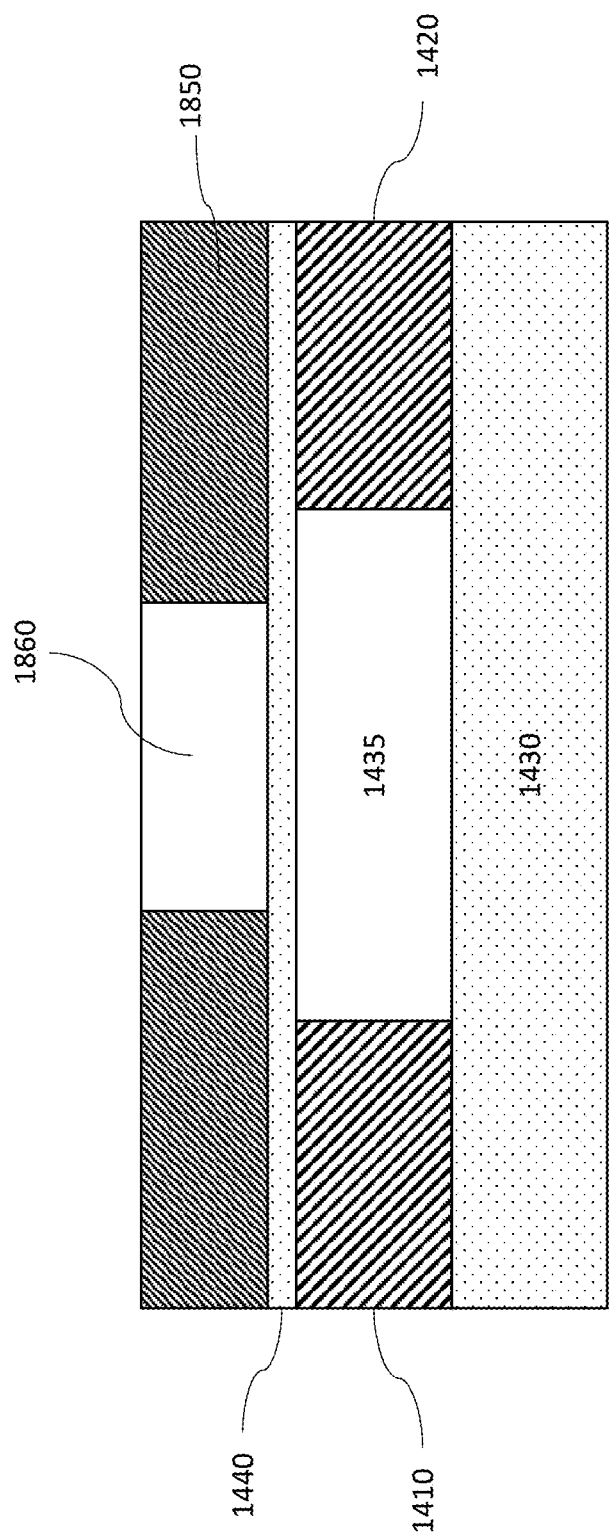
FIG. 18 is a schematic of a dynamically tunable optical antenna.

FIG. 18 illustrates that the optical antenna can be dynamically tunable, where lateral p-type and n-type junctions beneath selective regions of the aluminum plate can alter the conductivity and loss to tune the effective patch-slot dimensions. In FIG. 18, the antenna 1850 has an aperture 1860 which may be a slot of any type as described in FIGS. 15-17. The device of FIG. 18 includes a p-region 1410, an n-region 1420, an NID silicon 1435, a GOX 1440, and a substrate (or insulator) 1430 as defined in FIG. 14.

Figure 19A:
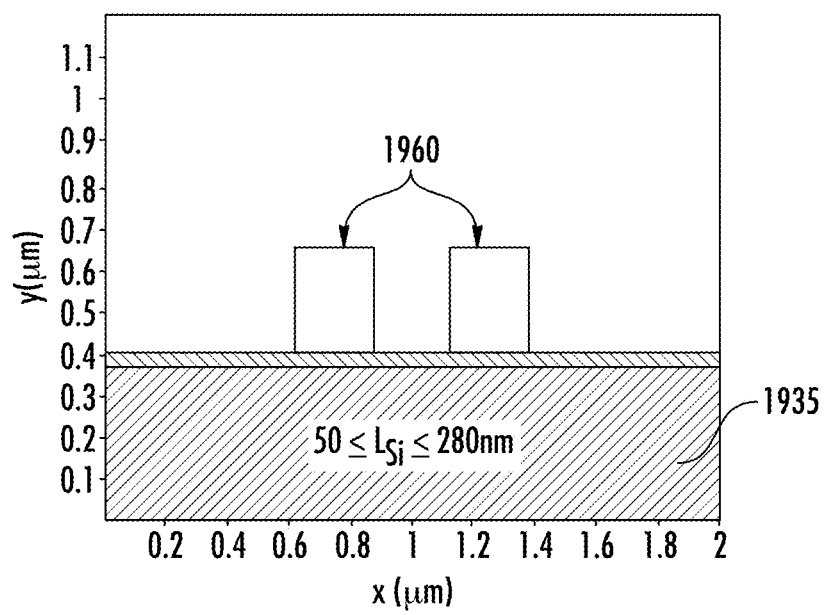
FIGS. 19A-19B illustrate an example CMOS patterned optical antenna in accordance with some embodiments.
Figure 19B:
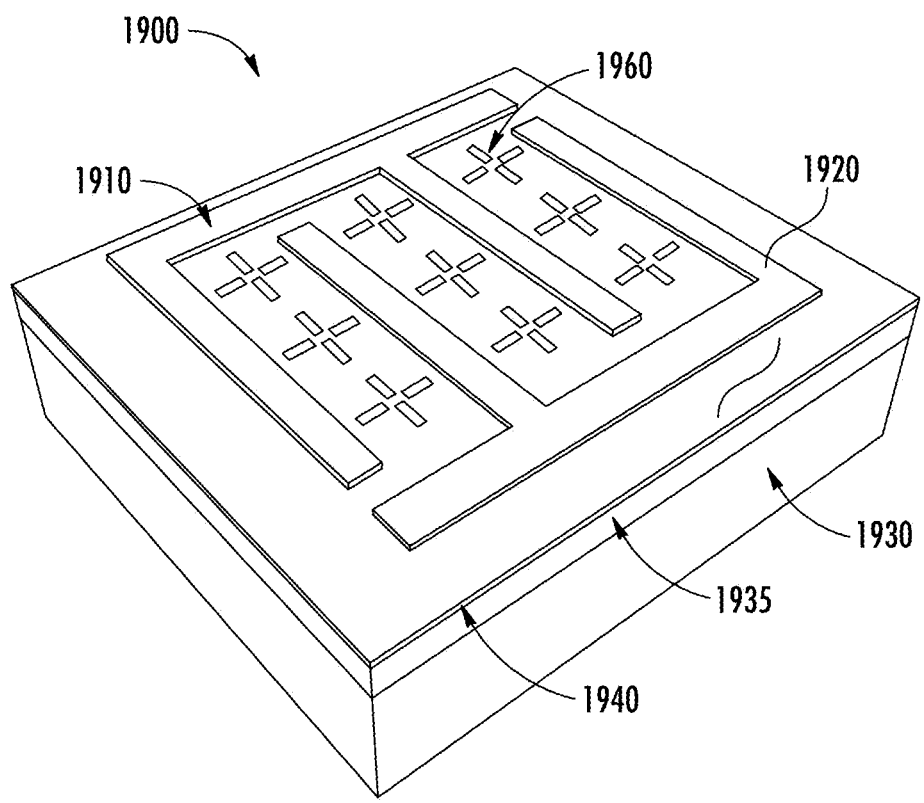

CMOS-patterned optical antennas are also possible, as an alternative method to lithographic patterning. For example, CMOS patterning can be utilized to fabricate pillar antenna structures on the plane of the planar optical antenna. FIGS. 19A-19B show an example of a half wavelength (λ/2) dipole enhanced UV SOS p-i-n detector, where FIG. 19A shows a vertical cross-section of λ/2 dipole Al antennas 1960 and FIG. 19B is a perspective view of an example biosensor device 1900 with the dipole antennas 1960. FIG. 19A illustrates that the antennas 1960 are configured as pillars with a rectangular vertical cross-sectional shape. The p-i-n detector device in this embodiment is constructed on an SOI or SOS platform 1930, with an active Si layer 1935 having a thickness (e.g., $t_{Si}$ of FIG. 14) from 50-280 nm, and a thermal gate oxide layer 1940. The antennas 1960 are configured in a cross-shape to provide polarization insensitivity. The antennas 1960 are made of aluminum to provide responsivity in the deep UV range, as described earlier. The p-type and n-type regions (1910 and 1920, respectively) are a lateral p-i-n detector, configured as interdigitated fingers in this embodiment.

Figure 20:
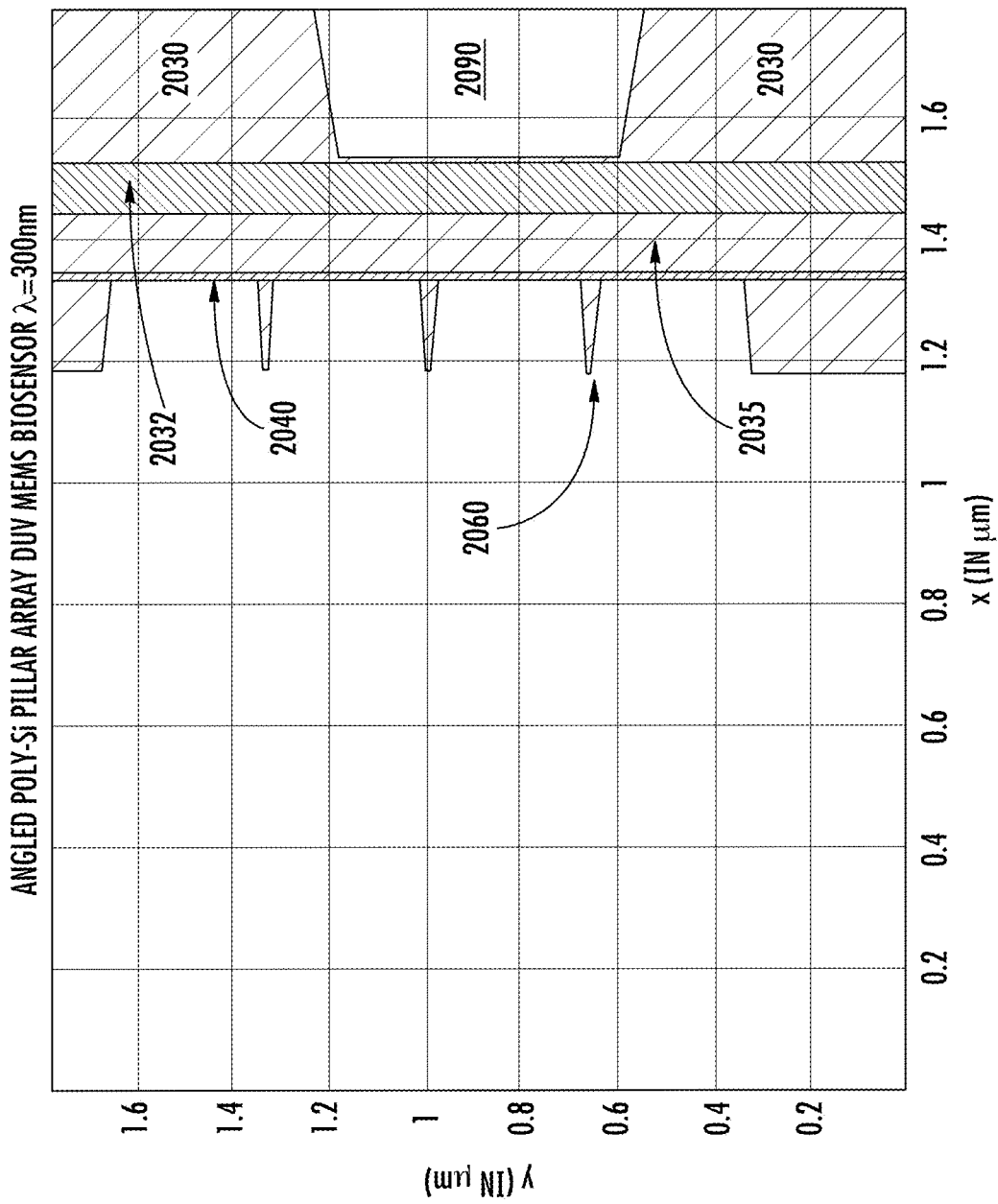
FIG. 20 illustrates another CMOS patterned optical antenna, in accordance with some embodiments.

FIG. 20 shows another embodiment of a CMOS-patterned antenna, utilizing an etched poly-Si nano-antenna array of monopoles 2060. The monopoles 2060 are configured as tapered/angled pillars, such as cones having a triangular vertical cross-sectional shape. The height, width, spacing and shaping (vertical cross-sectional shapes) of the monopoles 2060 may be tuned for the desired wavelength that is to be detected. Three monopoles 2060 are shown in the embodiment of FIG. 20, but fewer or more monopoles may be used in other embodiments. The detector includes substrate 2030, buried oxide layer 2032, fully-depleted silicon layer 2035, gate oxide layer 2040, and optional via 2090.

Figure 21:
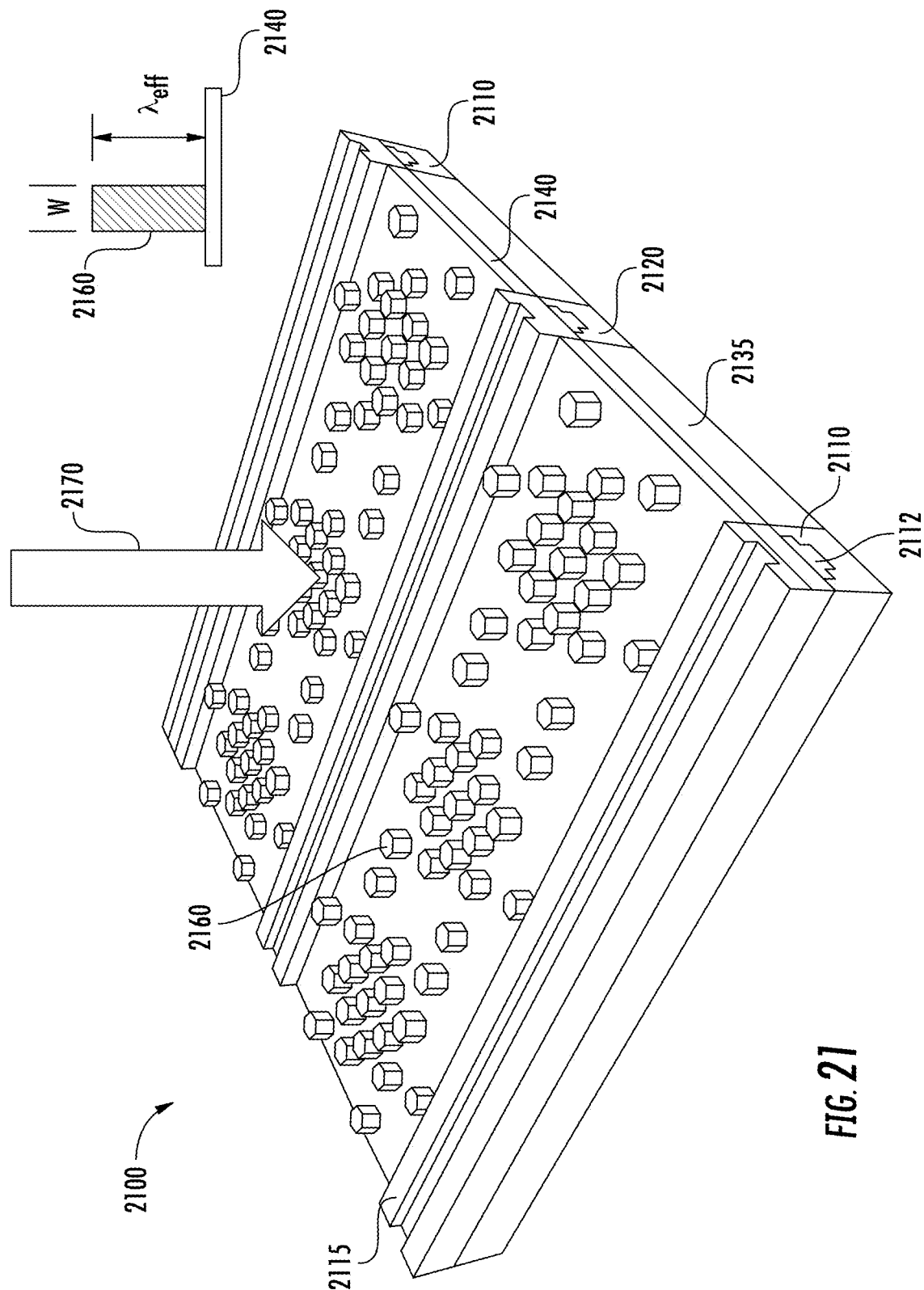
FIG. 21 is a perspective view of a biosensor using vertical monopole antennas, in accordance with some embodiments.
Figure 22:
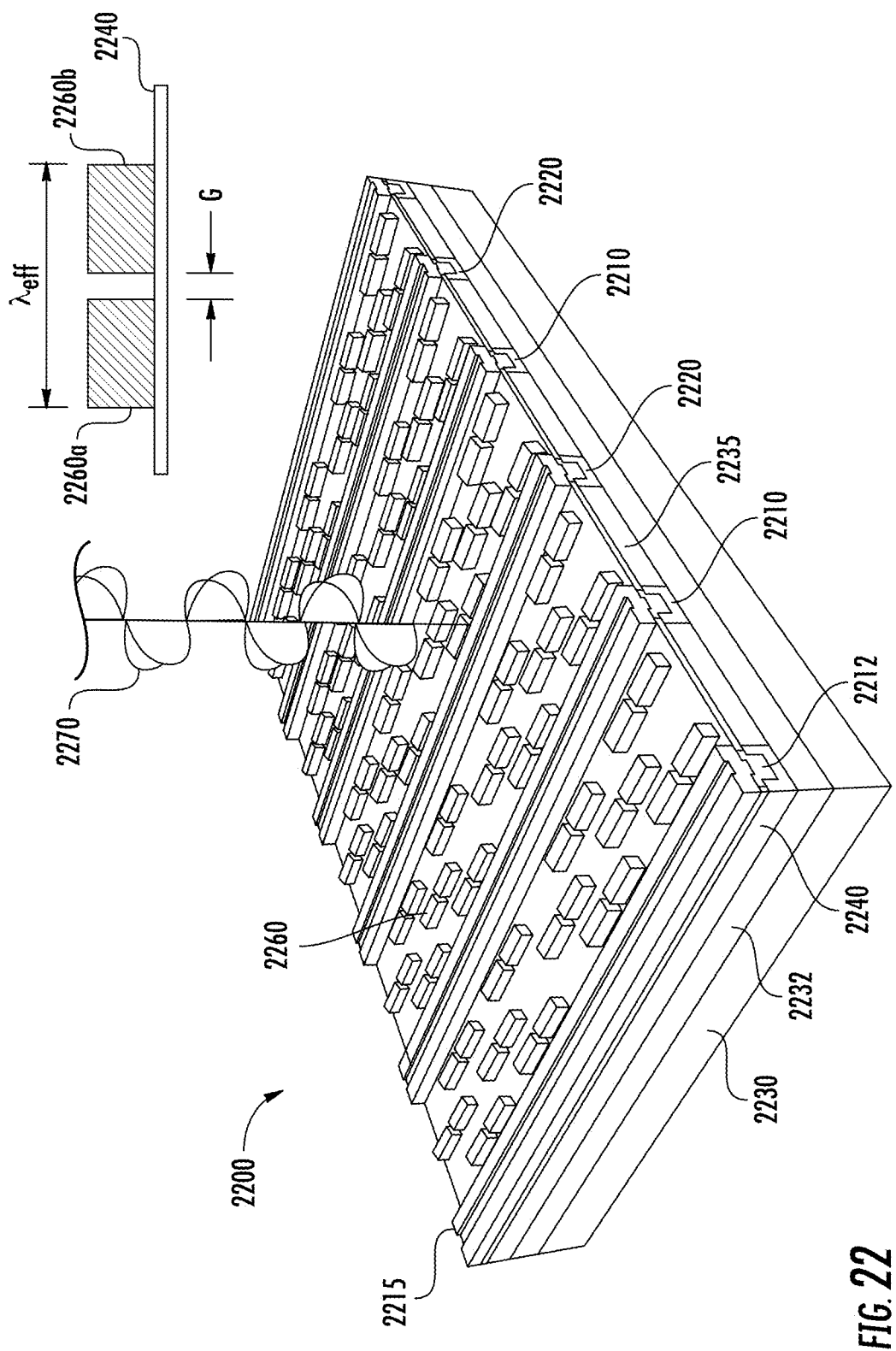
FIG. 22 is a perspective view of a biosensor using vertical dipole antennas, in accordance with some embodiments.

FIGS. 21 and 22 are perspective views of fluorescent biosensors using vertical monopole and lateral dipole antennas, respectively. Biosensor 2100 of FIG. 21 includes p-well 2110, n-well 2120, an intrinsic fully-depleted silicon layer 2135, a gate oxide layer 2140, and aluminum metal wavelength monopoles 2160. The p-doped and n-doped regions 2110 and 2120 each have a contact 2112 such as TiN, and IDT metallization 2115 (e.g., aluminum). The biosensor is exposed to fluorescence 2170 of wavelength λ. The monopole antennas 2160 are configured as pillars with hexagonal cross-sections in this embodiment. The width W and height $\lambda_{\textit{eff}}$ of the monopole antennas 2160 can be tuned according to the wavelength being detected.

The device 2200 of FIG. 22 has lateral dipole antennas 2260, where each aluminum metal wavelength (λ/2) antenna 2260 has two portions 2260a and 2260b that are laterally spaced apart by a dipole separation distance G. The overall length of the antenna 2260 is $\lambda_{\textit{eff}}$. Biosensor 2200 includes p-wells 2210, n-wells 2220, a silicon or sapphire substrate 2230, a buried oxide layer 2232, an intrinsic fully-depleted silicon layer 2235, and a gate oxide layer 2240. The p-doped and n-doped regions 2210 and 2220 each have a contact 2212 (e.g, TiN), and IDT metallization 2215 (e.g., aluminum). The biosensor 2200 is exposed to fluorescence 2270 of wavelength λ. The dipole separation G and length $\lambda_{\textit{eff}}$ of FIG. 22 can be tuned according to the wavelength being detected. FIGS. 21 and 22 illustrate that the pillars may be arranged in various patterns to achieve the desired tuning, and also polarization insensitivity.

As demonstrated by FIGS. 13-22, the spectral response of the sample under test can be optimized using various approaches such as: lithographically patterning poly-Si on the GOX to tune the wavelength selectivity of the device; optimizing the poly-Si lossy monopole feature (e.g., sidewall, width/poly, length/poly) along with the air gap spacing for a specific wavelength; fabricating multiple lateral p-i-n on the die for a plurality of specific wavelength responses and thus forming a planar spectrometer. In some embodiments, the optical antenna can be made of CMOS compatible materials such as poly-Si on GOX, Al/GOX, and Al/poly/GOX. In other embodiments, the optical antenna can use magnetic materials such as Ni, s.t. u(x,y)>1.

In embodiments of the ultraviolet fluorescence detector, various benefits are presented. High sensitivity detectors having spectral selectivity may be built. Multiple lateral pins/dies with selective wavelength response enable in-situ spectroscopy. Integration of TIA and preprocessing spectral signal is possible using SOS and SOI analog/digital cores. Spectral fusion on chip enables single chip spectrometer for bacterial detection. Lab-on-a-chip (LOC) for selective DNA processing is made possible. III-N photo detection suffers sensitivity compared to UV Si pin and lack of standard processes for integration in complex spectrometer. The indirect bandgap of Si enables low noise and APD implementation.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those of ordinary skill in the art, without departing from the scope of the present invention. Furthermore, those of ordinary skill in the art will appreciate that the foregoing description is by way of example only, and is not intended to limit the invention.

Thus, it is intended that the present subject matter covers such modifications and variations.

What is claimed is:

1. A semiconductor biosensor comprising:
   a plurality of wells, each well configured to hold a test sample and to allow the test sample to be irradiated with ultraviolet radiation;
   a plurality of detectors configured to capture a spectral response of the test sample irradiated with the ultraviolet radiation, wherein each well in the plurality of wells is located directly on a detector in the plurality of detectors, wherein each detector comprises a planar optical antenna on a photodiode, with the well directly on the planar optical antenna, and wherein the planar optical antenna is tuned to a particular wavelength; and
   a processing circuitry coupled to the plurality of detectors, the processing circuitry being configured to calculate an average spectral response for the plurality of detectors.

2. The biosensor of claim 1 wherein the plurality of wells, the plurality of detectors, and the processing circuitry are integrated on a single chip.

3. The biosensor of claim 1 wherein:
   the plurality of detectors is grouped into a first set of detectors in a first pixel of the biosensor and second set of detectors in a second pixel of the biosensor;
   the planar optical antennas of the first set of detectors in the first pixel are tuned to a first wavelength; and
   the planar optical antennas of the second set of detectors in the second pixel are tuned to a second wavelength different from the first wavelength.

4. The biosensor of claim 1 wherein the spectral response is created in an absorption mode or an excitation fluorescence mode.

5. The biosensor of claim 1 wherein each photodiode comprises a lateral p-i-n diode.

6. The biosensor of claim 1 wherein for each detector in the plurality of detectors, the planar optical antenna is configured to filter the spectral response from the test sample to the photodiode.

7. The biosensor of claim 1 wherein at least one planar optical antenna in the plurality of detectors comprises a metal or a dielectric material.

8. The biosensor of claim 3 wherein the processing circuitry compiles signals received from the first set of detectors and the second set of detectors into an output spectrum.

9. The biosensor of claim 1 wherein at least one planar optical antenna in the plurality of detectors comprises a structure having dimensions configured to tune the at least one planar optical antenna to the particular wavelength.

10. The biosensor of claim 9 wherein:
    the at least one planar optical antenna comprises aluminum;
    the particular wavelength to which the at least one planar optical antenna is tuned is in a range of 180-400 nm;
    the structure is an aperture;
    the aperture is chosen from the group consisting of: single slots, grouped slots, and patches; and
    the dimensions comprise a length, a width and a height of the aperture.

11. The biosensor of claim 9 wherein:
    the at least one planar optical antenna comprises aluminum;
    the particular wavelength to which the at least one planar optical antenna is tuned is in a range of 180-400 nm;
    the structure is a pillar;
    the pillar is a monopole or dipole antenna; and
    the dimensions comprise a height and a width of the pillar, and a vertical cross-sectional shape of the pillar.

12. The biosensor of claim 1 wherein at least one planar optical antenna in the plurality of detectors comprises a plurality of structures having a positional arrangement configured for polarization insensitivity.

13. The biosensor of claim 12 wherein the structures comprise a plurality of slots, and wherein the positional arrangement configured for polarization insensitivity comprises a first group of the plurality of slots being orthogonal to a second group of the plurality of slots.

14. A biosensing device comprising:
    a plurality of wells, wherein each well is configured to hold a test sample and to allow the test sample to be irradiated with ultraviolet radiation; and
    a plurality of detectors, each detector comprising a) a photodiode and b) a planar optical antenna on the photodiode;
    wherein each well is located directly on the planar optical antenna of a corresponding one of the plurality of detectors; and
    wherein each planar optical antenna has a structure in or on a plane of the planar optical antenna, the structure having dimensions configured to tune the planar optical antenna to a particular wavelength.

15. The device of claim 14 wherein:
    each planar optical antenna comprises aluminum, and the particular wavelength to which the planar optical antenna is tuned is in a range of 180-400 nm;
    the structure is an aperture;
    the aperture is chosen from the group consisting of: single slots, grouped slots, and patches; and
    the dimensions comprise a length, a width and a height of the aperture.

16. The device of claim 14 wherein:
    each planar optical antenna comprises aluminum, and the particular wavelength to which the planar optical antenna is tuned is in a range of 180-400 nm;
    the structure is a pillar;
    the pillar is a monopole or dipole antenna; and
    the dimensions comprise a height and a width of the pillar, and a vertical cross-sectional shape of the pillar.

17. The device of claim 14 wherein the structure comprises a plurality of the structures, having a positional arrangement configured for polarization insensitivity.

18. The device of claim 17 wherein the plurality of structures is a plurality of slots, and wherein the positional arrangement configured for polarization insensitivity comprises a first group of the plurality of slots being orthogonal to a second group of the plurality of slots.

19. The device of claim 14 wherein the device is absent of a wavelength spatially dispersive element between the well and the detector.

* * * * *